(12) United States Patent
Yokoyama et al.

(10) Patent No.: US 10,379,111 B2
(45) Date of Patent: Aug. 13, 2019

(54) TARGET SUBSTANCE CAPTURING DEVICE

(71) Applicant: NSK LTD., Tokyo (JP)

(72) Inventors: Keisuke Yokoyama, Kanagawa (JP);
Hideki Furukawa, Kanagawa (JP);
Nobuko Okutani, Kanagawa (JP);
Kunihiko Sasao, Kanagawa (JP);
Toshiaki Oguchi, Kanagawa (JP)

(73) Assignee: NSK LTD., Tokyo (JP)

( * ) Notice: Subject to any disclaimer, the term of this patent is extended or adjusted under 35 U.S.C. 154(b) by 82 days.

(21) Appl. No.: 14/783,671

(22) PCT Filed: Mar. 31, 2014

(86) PCT No.: PCT/JP2014/059591
§ 371 (c)(1),
(2) Date: Oct. 9, 2015

(87) PCT Pub. No.: WO2014/168041
PCT Pub. Date: Oct. 16, 2014

(65) Prior Publication Data
US 2016/0061823 A1  Mar. 3, 2016

(30) Foreign Application Priority Data

Apr. 12, 2013 (JP) .................................. 2013-084190
Jan. 27, 2014 (JP) .................................. 2014-011964

(51) Int. Cl.
*G01N 33/53* (2006.01)
*G01N 21/75* (2006.01)
(Continued)

(52) U.S. Cl.
CPC ....... *G01N 33/5302* (2013.01); *G01N 21/553* (2013.01); *G01N 21/554* (2013.01);
(Continued)

(58) Field of Classification Search
CPC .... G01N 33/5302; G01N 21/01; G01N 21/41; G01N 21/553; G01N 21/75
(Continued)

(56) References Cited

U.S. PATENT DOCUMENTS

2006/0119853 A1   6/2006 Baumberg et al.
2007/0009219 A1*  1/2007 Hatsuda ................. B82Y 20/00
                                                   385/129

(Continued)

FOREIGN PATENT DOCUMENTS

CN       1514520 A     7/2004
CN     101057132 A    10/2007
(Continued)

OTHER PUBLICATIONS

Kelf, T.A. (2006). "Localized and delocalized plasmons in metallic nano-voids." Physical Review B. 74, 245415.*
(Continued)

*Primary Examiner* — Jill A Warden
*Assistant Examiner* — Jacqueline Brazin
(74) *Attorney, Agent, or Firm* — Sughrue Mion, PLLC

(57) ABSTRACT

A target substance capturing device includes a reflection surface on which a plurality of non-flat portions is arrayed, the reflection surface capturing a target substance, and reflecting irradiated light. The plurality of non-flat portions are arranged in an array, the array includes a plurality of unit arrays in which the plurality of non-flat portions are arranged such that each one center of the non-flat portions superposes a position of a vertex in an M-time symmetrical figure, and the plurality of unit arrays is arranged such that each one center of gravity of the M-time symmetrical figure superposes a position of an intersection of an N-time sym-
(Continued)

metrical lattice pattern, where M is an integer of two or more, and N is an integer of two or more and different from M.

7 Claims, 20 Drawing Sheets

(51) Int. Cl.
    *G01N 21/552*     (2014.01)
    *G01N 21/77*     (2006.01)
    *B82Y 5/00*     (2011.01)

(52) U.S. Cl.
    CPC .......... *G01N 21/75* (2013.01); *G01N 21/7743* (2013.01); *B82Y 5/00* (2013.01); *G01N 2021/757* (2013.01)

(58) Field of Classification Search
    USPC ........................................................ 422/553
    See application file for complete search history.

(56) References Cited

U.S. PATENT DOCUMENTS

| | | | |
|---|---|---|---|
| 2009/0116033 A1* | 5/2009 | Wang | B82Y 20/00 356/481 |
| 2009/0153866 A1 | 6/2009 | Yamamichi et al. | |
| 2009/0263094 A1* | 10/2009 | Noda | B82Y 20/00 385/129 |
| 2009/0273779 A1 | 11/2009 | Baumberg et al. | |
| 2011/0249259 A1 | 10/2011 | Van Dorpe et al. | |
| 2012/0038926 A1* | 2/2012 | Endo | B82Y 20/00 356/445 |
| 2012/0251035 A1 | 10/2012 | Hsu et al. | |
| 2012/0257204 A1* | 10/2012 | Walters | C12Q 1/6837 356/445 |

FOREIGN PATENT DOCUMENTS

| | | |
|---|---|---|
| CN | 101405634 A | 4/2009 |
| CN | 102709416 A | 10/2012 |
| JP | 2008-519254 A | 6/2008 |
| JP | 2009-222401 A | 1/2009 |
| JP | 2011-252928 A | 12/2011 |
| JP | 2012-511705 A | 5/2012 |
| KR | 1020100114622 * | 10/2010 |
| WO | 2010/044274 A1 | 4/2010 |

OTHER PUBLICATIONS

T.A. Kelf et al., "Localized and delocalized plasmons in metallic nanovoids", Physical Review B, Dec. 13, 2006, vol. 74, p. 245415_1-245415_12.
Japanese Office Action of JP2014-517277 dated Feb. 18, 2015.
Japanese Office Action of JP2014-517277 dated Sep. 2, 2015.
Kohei Nakamoto et al, "Development of a mass-producible on-chip plasmonic nanohole array biosensor", The Royal Society of Chemistry, Nanoscale, Sep. 2011, 3, p. 5067-5075.
Molly M. Miller et al., "Sensitivity of Metal Nanoparticle Surface Plasmon Resonance to the Dielectric Environment", Journal of Physical Chemistry B, Oct. 21, 2005, p. 21556-21565, No. 109.
International Search Report of PCT/JP2014/059591 dated Jun. 17, 2014.
Communicaton dated Jan. 24, 2017, from the State Intellectual Property Office of People's Republic of China in counterpart Application No. 201480000573.2.

* cited by examiner

TARGET SUBSTANCE CAPTURING DEVICE

CROSS REFERENCE TO RELATED APPLICATIONS

This is a National Stage of International Application No. PCT/JP2014/059591 filed Mar. 31, 2014, claiming priority based on Japanese Patent Application Nos. JP2013-084190 filed Apr. 12, 2013 and JP2014-011964 filed Jan. 27, 2014, the contents of all of which are incorporated herein by reference in their entirety.

BACKGROUND OF THE INVENTION

Field of the Invention

The present invention relates to a target substance capturing device that detects a target substance.

Description of the Related Art

As means to detect a target substance such as protein or a cell, or to measure the concentration, biosensors using a photonic crystal are known (for example, Non Patent Literature 1 (hereinafter, Prior Art 2)). The biosensors described in Prior Art 2 irradiate a photonic crystal substrate on which a gold thin film is formed, with light, and measure reflected light reflected at the photonic crystal substrate, thereby to detect the target substance, measure the concentration of the target substance, and the like. Patent Literature 1 (herein after, Prior Art 1) describes a biosensor having a reflection surface on which columnar protruding portions are uniformly arrayed in a square lattice shape, that is, in an arrangement having one rotational symmetry, as an uneven structure. Non Patent Literature 2 (hereinafter, Prior Art 3) describes a sensitivity figure of merit FOM1 and a sensitivity figure of merit FOM2, as performance indexes of sensitivity.

PRIOR ART

Prior Art 1 (Patent Literature 1): WO 2010/044274 A

Prior Art 2 (Non Patent Literature 1): "Development of a mass-producible on-chip plasmonic nanohole array biosensor": Kohei Nakamoto, Ryoji Kurita, Osamu Niwa, Toshiyuki Fujiicd and Munehiro Nishida, Received 20 Jul. 2011, Accepted 27 Sep. 2011

Prior Art 3 (Non Patent Literature 2): "Sensitivity of Metal Nanoparticle Surface Plasmon Resonance to the Dielectric Environment": Journal of Physical Chemistry B, 109(46), P21556-21565

The biosensor described in Prior Art 2 includes a reflection surface on which recessed portions are arrayed in a triangular lattice shape. To enhance sensor sensitivity, a biosensor typically requires a large number of recessed portions. Further, a wavelength with which reflected light of light incident on the reflection surface exhibits an extreme value depends on a cycle of a lattice pattern of the reflection surface. To easily identify the wavelength, it is preferable that the cycle of a lattice pattern of the reflection surface can be a desired value. However, if the number of the recessed portions is simply increased, the cycle of a lattice pattern of the reflection surface becomes small. Therefore, a biosensor that can enhance the sensor sensitivity while causing the cycle of a lattice pattern of the reflection surface to be a desired value is desired.

An objective of the present invention is to provide a target substance capturing device that can enhance sensor sensitivity while causing a cycle of a lattice pattern of a reflection surface to be a desired value, and a target substance detecting device including the target substance capturing device.

SUMMARY OF THE INVENTION

According to an aspect of the invention, a target substance capturing device comprises a reflection surface on which a plurality of non-flat portions is arrayed, the reflection surface capturing a target substance, and reflecting irradiated light. The plurality of non-flat portions are arranged in an array, the array includes a plurality of unit arrays in which the plurality of non-flat portions is arranged such that each one center of the non-flat portions superposes a position of a vertex in an M-time symmetrical figure, and the plurality of unit arrays is arranged such that each one center of gravity of the M-time symmetrical figure superposes a position of an intersection of an N-time symmetrical lattice pattern, where M is an integer of two or more, and N is an integer of two or more and different from M.

The target substance capturing device according to the present invention has the unit arrays arrayed in a lattice shape. In a biosensor using a photonic crystal, a wavelength with which reflected light of light incident on a reflection surface exhibits an extreme value depends on a cycle of a lattice pattern of the reflection surface. Therefore, in the target substance capturing device according to the present invention, the wavelength of the reflected light that exhibits an extreme value depends on the cycle of a lattice pattern formed by the unit arrays. Further, since the unit array includes a plurality of non-flat portions, the number of the non-flat portions as the entire reflection surface increases, compared with a case where a similar lattice pattern is formed of non-flat portions. Therefore, the target substance capturing device according to the present invention can enhance the sensor sensitivity while causing the cycle of a lattice pattern of the reflection surface to be a desired value.

According to further aspect of the invention, a minimum distance between the centers of the non-flat portions in one unit array is from 0.4 times to 0.6 times (both inclusive) a minimum distance between the intersections of the lattice pattern. The minimum distance between centers of the non-flat portions in the one unit array is from 0.4 times to 0.6 times (both inclusive) the minimum distance between intersections of the lattice pattern, whereby the reflection surface can increase the number of the non-flat portions while maintaining the non-flat portions to have a predetermined size. Therefore, a specific surface area of the reflection surface becomes large.

According to further aspect of the invention, all of the non-flat portions belong to any of the unit arrays, and the non-flat portions belonging to one unit array are different from the non-flat portions belonging to an adjacent unit array. Accordingly, the target substance capturing device according to the present invention can decrease a possibility that the non-flat portions form the lattice pattern. Therefore, the target substance capturing device according to the present invention can enhance the sensor sensitivity while more reliably causing the cycle to be a desired value.

According to another aspect of the invention, the M is three, and the N is six. Each of the non-flat portions is arrayed on each vertex of a regular triangle in a unit array, where M is 3. The unit arrays are arrayed in a triangular lattice shape, where N is 6. Accordingly, the target substance capturing device according to the present invention can decrease a possibility that the non-flat portions form the lattice pattern, due to a positional relationship among the non-flat portions belonging to different unit arrays. Therefore, the target substance capturing device according to the present invention can enhance the sensor sensitivity while more reliably causing the cycle to be a desired value.

According to further aspect of the invention, a minimum distance between the centers of the non-flat portions in one unit array is 0.5 times a minimum distance between the intersections of the lattice pattern. Accordingly, in the target substance capturing device according to the present invention, the non-flat portions are arranged in a direction of the lattice pattern at regular intervals, so that the cycle of a lattice pattern is less likely to be disordered. Therefore, a half-value width of the shape of a spectrum of the reflected light becomes small, and a noise in measurement can be decreased. Therefore, an S/N ratio is improved, and the target substance capturing device according to the present invention can enhance the sensor sensitivity.

According to another aspect of the invention, a target substance capturing device that captures a target substance with a biosensor using a photonic crystal includes a reflection surface that reflects irradiated light, and has a plurality of non-flat portions arrayed on the reflection surface according to a fixed rule. An array in which the plurality of non-flat portions is arranged includes a plurality of unit arrays in which the non-flat portions are arranged such that each one center of the non-flat portions superposes a position of a vertex of a regular triangle. And in the array in which the plurality of non-flat portion is arranged, the plurality of unit arrays is arranged such that each one center of gravity of the regular triangle superposes an intersection of a lattice pattern, the lattices intersecting with each other at an angle of 60°.

Further, in the present invention, it is preferable that a diameter of a cross section of the non-flat portion is less than one time the C1, where a length of one side of the regular triangle is the C1. Further, the non-flat portion does not necessarily have a circular cross section shape, and may have a hexagonal or star-shaped cross section shape.

In the biosensor using a photonic crystal having a surface on which microstructures are arrayed according to a fixed rule, a wavelength with which reflected light of light incident on a reflection surface of a measuring portion exhibits an extreme value depends on a cycle of a lattice pattern of the reflection surface. Therefore, in the target substance capturing device according to the present invention, the wavelength with which reflected light exhibits an extreme value depends on a cycle of a lattice pattern formed by the unit arrays. Further, since the unit array includes a plurality of non-flat portions, the number of non-flat portions as the entire reflection surface increases, compared with a case where non-flat portions form a similar lattice pattern. Therefore, the target substance capturing device according to the present invention can enhance the sensor sensitivity while causing the cycle of a lattice pattern of the reflection surface to be a desired value.

In the target substance capturing device according to the present invention, the array of the plurality of non-flat portions includes a plurality of unit arrays in which the non-flat portions are arranged such that each one center of the non-flat portions superposes a position of a vertex of a regular triangle, and the unit arrays are arranged such that each one center of gravity of the regular triangle superposes a position of an intersection of a lattice pattern, the lattices intersecting with each other at an angle of 60°. With such arrangement, the array of the non-flat portions includes only six-time rotational symmetry in the entire sensor, and one peak appears in a spectrum of reflected light. Therefore, the amount of a target substance can be measured in higher accuracy than an arrangement including a plurality of rotational symmetries.

According to further aspect of the invention, a cross section of the non-flat portion along the reflection surface is circle, and a diameter of the cross section of the non-flat portion is one time or less a length of one side of the regular triangle. Accordingly, the adjacent non-flat portions become not in contact with each other. Therefore, the shape of the non-flat portion can be easily kept.

According to further aspect of the invention, a length of one side of the regular triangle is 0.5 times a minimum distance between the intersections of the lattice pattern, and the one side of the regular triangle is parallel to a straight line included in the lattice pattern. Accordingly, non-flat portions 28A are arranged in a direction of a lattice pattern La at regular intervals, so that a cycle of the lattice pattern La is less likely to be disordered. Therefore, a half-value width of the shape of a spectrum of the reflected light becomes small, and a noise in measurement can be decreased. Therefore, the S/N ratio can be improved, and the target substance capturing device can enhance the sensor sensitivity.

According to further aspect of the invention, a cross section of the non-flat portion along the reflection surface is a regular hexagon or a star shape. The shape of the cross section has six-time rotational symmetry. Therefore, by causing the non-flat portion to have such a shape, the target substance capturing device according to the present invention can realize further improvement of measurement accuracy because the shape of the non-flat portion has six-time symmetry, in addition to the arrangement of the non-flat portions is the six-time symmetry.

By use of the target substance capturing device of the present invention, the sensor sensitivity can be enhanced while the cycle of the lattice pattern of the reflection surface can be a desired value. The target substance detecting device including the target substance capturing device of the present invention can enhance the sensor sensitivity while causing the cycle of the lattice pattern of the reflection surface to be a desired value.

BRIEF DESCRIPTION OF THE DRAWINGS

FIG. 32A is a diagram illustrating a non-flat portion having a hexagonal cross section and FIG. 32B is a diagram illustrating a non-flat portion having a star-shaped cross section.

DETAILED DESCRIPTION OF THE PREFERRED EMBODIMENT

Hereinafter, embodiments for implementing a target substance detecting device according to the present invention (hereinafter, referred to as embodiments) will be explained in detail based on the drawings. Note that the present invention is not limited by the embodiments described below. Configuration elements of the embodiments below include those that can be easily assumed by persons skilled in the art, those that are substantially identical, and those in a scope of so-called equivalents. Further, the configuration elements disclosed in the embodiments below can be appropriately combined.

[First Embodiment]
<Target Substance Detecting Device>

Figure 1:
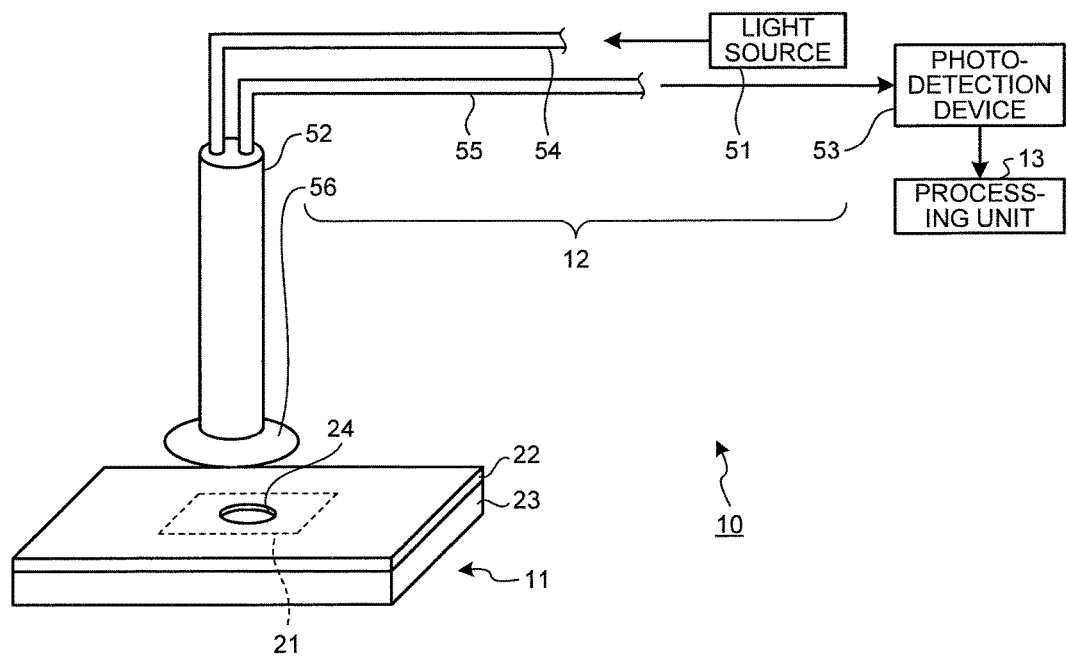
FIG. 1 is a diagram illustrating a target substance detecting device.

A target substance detecting device including a target substance capturing device according to a first embodiment will be explained. FIG. 1 is a diagram illustrating a target substance detecting device. A target substance detecting device 10 includes a photonic crystal biosensor (target substance capturing device) 11 according to the first embodiment, a photo-detection section 12, and a processing unit 13.

(Photonic Crystal Biosensor)

First, the photonic crystal biosensor 11 will be explained. The photonic crystal biosensor 11 includes a metal-film coated photonic crystal 21, an upper plate 22, and a lower plate 23. The upper plate 22 is provided with an opening 24. In the first embodiment, the photonic crystal biosensor 11 has a structure in which the metal-film coated photonic crystal 21 is sandwiched by the upper plate 22 and the lower plate 23. Note that, in the first embodiment, the photonic crystal biosensor 11 is formed to include the upper plate 22 and the lower plate 23. However, an embodiment is not limited to the structure, and may be formed of the metal-film coated photonic crystal 21 only.

(Metal-Film Coated Photonic Crystal)

Figure 2:
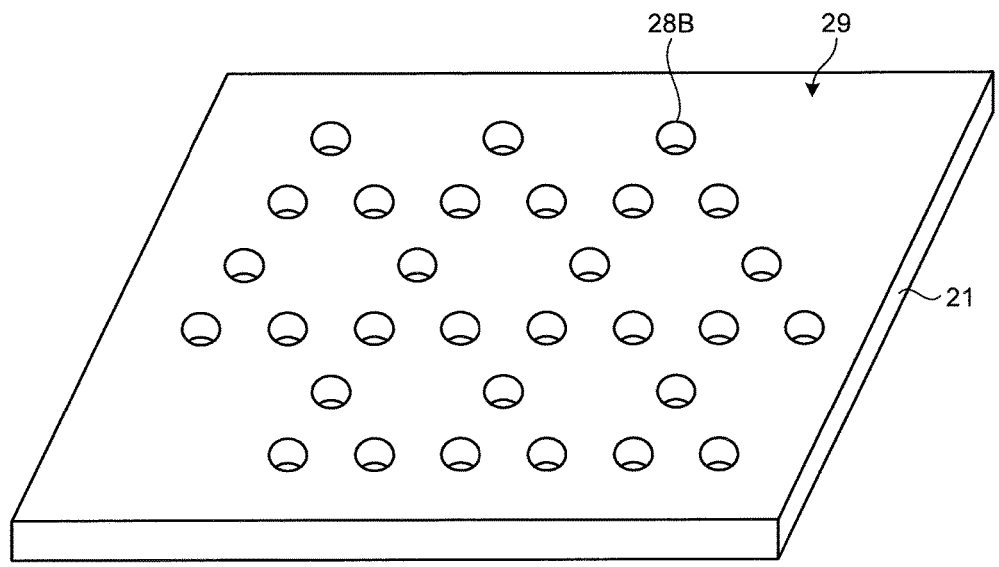
FIG. 2 is a perspective view of a metal-film coated photonic crystal.
Figure 3:
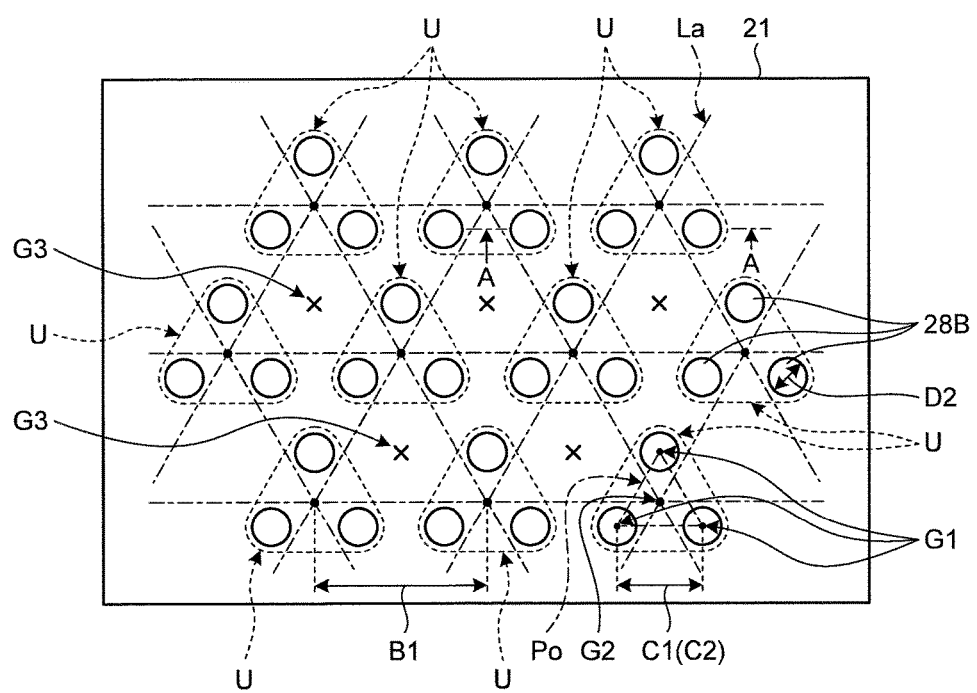
FIG. 3 is a plan view of a metal-film coated photonic crystal.
Figure 4:
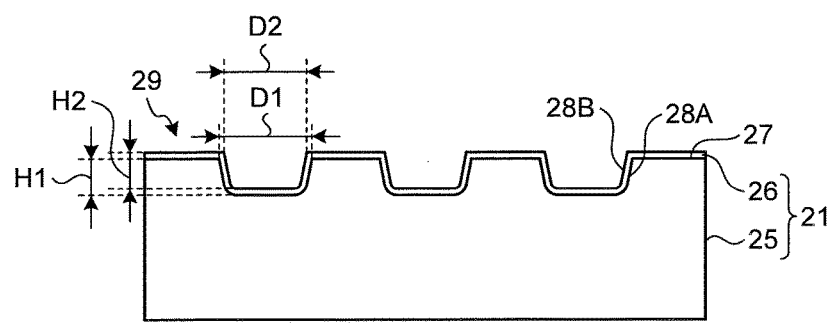
FIG. 4 is a diagram illustrating an A-A cross section in FIG. 3.

FIG. 2 is a perspective view of the metal-film coated photonic crystal 21. FIG. 3 is a plan view of the metal-film coated photonic crystal 21. FIG. 4 is a diagram illustrating the A-A cross section in FIG. 3, and illustrates a cross section of when a photonic crystal 25 is cut in a plane perpendicular to a surface 27 of the photonic crystal 25. Note that FIGS. 2 to 4 are schematically illustrated diagrams, and the thickness, the size, and the like of components that configure the metal-film coated photonic crystal 21 are different from actual thickness and size. Hereinafter, the same applies to the first embodiment and other embodiments described below. As illustrated in FIGS. 2 to 4, the metal-film coated photonic crystal 21 includes the photonic crystal 25 and a metal film 26. The metal-film coated photonic crystal 21 has a structure in which a reflection surface 29 obtained such that a plurality of non-flat portions 28A is arrayed in the surface 27 of the photonic crystal 25 is coated with the metal film 26. The non-flat portion 28A is a columnar recessed portion depressed in the surface 27.

First, the photonic crystal 25 will be explained. Typically, the photonic crystal is a structure that has a reflection surface having a surface where recessed portions having a predetermined depth or protruding portions having a predetermined height are cyclically formed, and can obtain reflected light when the reflection surface is irradiated with light having a specific wavelength (parallel light). The structure that can obtain the reflected light having a specific wavelength when the reflection surface having a surface where recessed portions or protruding portions are cyclically formed is irradiated with the light is typically called photonic crystal.

The photonic crystal is a structure having a lattice structure with a subwavelength interval. When a surface of the structure (hereinafter, referred to as reflection surface) is irradiated with light having a wide region wavelength, the photonic crystal reflects or transmits light in a specific wavelength band, depending on a surface state of the photonic crystal. The surface state of the photonic crystal depends on the shape or the material of the photonic crystal, for example. By reading change of the reflected light or the transmitted light, change of the surface state of the photonic crystal can be quantified. Examples of the change of the surface state of the photonic crystal include absorption of a substance to the surface, and structure change. When the photonic crystal having a surface on which a metal thin film is formed is irradiated with light, an extreme value (a maximum value or a minimum value) appears in reflectance of light or transmittance of light. The extreme value of the reflectance or the transmittance depends on a type of the metal, a film thickness of the metal, and the shape of the surface of the photonic crystal. By reading the reflectance of light or the transmittance of light, the change of the surface state of the photonic crystal can be quantified. The metal thin film will be explained below. To quantify the change of the surface state of the photonic crystal from the change of the reflected light or the transmitted light, the following method can be used. For example, a change amount of the reflectance or the transmittance in the extreme value (a maximum value or a minimum value), or a shift amount of a wavelength with which the reflectance or the transmittance becomes the extreme value is obtained. Note that, when there is a plurality of extreme values of the reflectance and the transmittance, an arbitrary extreme value is focused. Then, the change amount of the focused extreme value or the shift amount of the wavelength with which the focused extreme value is obtained is obtained, so that the change of the surface state of the photonic crystal can be quantified.

As illustrated in FIGS. 2 to 4, the photonic crystal 25 includes the reflection surface 29 having the surface 27 on which the plurality of non-flat portions 28A is arrayed. When the reflection surface 29 is irradiated with light, light that has a specific wavelength depending on the shape and the material of the photonic crystal 25 is reflected.

In the first embodiment, an array in which the plurality of non-flat portions 28A is arranged includes a plurality of unit arrays U in which three non-flat portions 28A are arranged such that each one center G1 of the non-flat portions 28A superposes a position of a vertex in regular triangle Po that is a three-time symmetrical figure. In the array in which the plurality of non-flat portions 28A is arranged, the plurality of unit arrays U is arranged such that each one center of gravity G2 of the regular triangle Po superposes a position of an intersection of a six-time symmetrical lattice pattern La. Accordingly, the unit arrays U are arranged to form the lattice pattern La. Here, the wavelength with which the reflected light of the light incident on the reflection surface 29 of the photonic crystal 25 exhibits the extreme value depends on a cycle of the lattice pattern La of the reflection surface 29. The cycle of the lattice pattern La is equal to a minimum distance B1 between the centers of gravity G2, on the reflection surface 29. Therefore, in the first embodiment, the wavelength with which the reflected light of the light incident on the reflection surface 29 exhibits the extreme value depends on the minimum distance B1 between the centers of gravity G2.

Further, since the unit array U includes the plurality of non-flat portions 28A, the number of the non-flat portions 28A as the entire reflection surface increases, compared with a case in which the non-flat portions 28A are arranged to form the lattice pattern La. Further, a distance C1 between the centers G1 of the non-flat portions 28A in the unit array U is preferably from 0.4 times to 0.6 times (both inclusive) the minimum distance B1 between the centers of gravity G2 that is equal to the minimum distance between the intersections of the lattice pattern La. Therefore, on the reflection surface 29, the number of the non-flat portions 28A can be increased without making the cycle of the lattice pattern La small, the cycle being the minimum distance B1 between the centers of gravity G2. Further, on the reflection surface 29, the number of the non-flat portions 28A per unit area increases while a diameter D1 of the non-flat portion 28A is kept to a desired size. Accordingly, the photonic crystal 25 of the first embodiment can enhance the sensitivity when used as a sensor, by an increase in a specific surface area of the reflection surface 29. Therefore, the sensor using the photonic crystal 25 of the first embodiment can enhance the sensor sensitivity while causing the cycle of the lattice pattern La of the reflection surface 29 to be a desired value.

Further, all of the non-flat portions 28A belong to any of the unit arrays U. The non-flat portions 28A belonging to one unit array U are different from the non-flat portions 28A belonging to an adjacent unit array U. Accordingly, the non-flat portion 28A is not arranged in a position G3 of FIG. 3, for example. Here, the position G3 is a position of a center of gravity of a triangle that is made by connecting the centers of gravity G2 of adjacent three regular triangles Po with line segments. In the photonic crystal 25 of the first embodiment, the non-flat portion 28A is not arranged alone. Therefore, the non-flat portion 28A does not form the lattice pattern La. Therefore, on the reflection surface 29, the number of the non-flat portions 28A can be increased without making the cycle of the lattice pattern La small, the cycle being the minimum distance B1 between the centers of gravity G2. Therefore, the sensor using the photonic crystal 25 of the first embodiment can enhance the sensor sensitivity while more reliably causing the cycle to be a desired value.

Further, the distance C1 between the centers G1 is preferably 0.5 times the minimum distance B1 between the centers of gravity G2. Accordingly, a possibility of an increase in the number of the non-flat portions per unit area on the reflection surface 29 increases. When the non-flat portions 28A are arranged in a direction of the lattice pattern La at regular intervals, on the reflection surface 29, the cycle of the lattice pattern La is less likely to be disordered. Therefore, a half-value width of the shape of a spectrum of the reflected light becomes small, and a noise in measurement can be decreased. Therefore, the sensor using the photonic crystal 25 of the first embodiment improves an S/N ratio, and can further enhance the sensor sensitivity.

Further, the number of the non-flat portions 28A included in the unit array U is not limited to be three. For example, the number of the non-flat portions 28A included in the unit array U may be four or more. Further, the position where the center G1 of the non-flat portion 28A superposes in the unit array U may not be the vertex of the regular triangle Po. For example, the position where the center G1 of the non-flat portion 28A superposes in the unit array U may be a vertex of a rotational symmetrical figure other than the regular triangle. Further, the position where the center of gravity G2 of the regular triangle Po superposes may not be the intersection of the six-time symmetrical lattice pattern La. For example, the position where the center of gravity G2 of the regular triangle Po superposes may be an intersection of a rotational symmetrical lattice pattern other than the six-time symmetrical lattice pattern. Note that M and N need to be different, where an integer of two or more is M, and an integer of two or more is N, and the position where the center G1 of the non-flat portion 28A superposes in the unit array U is a vertex of a M-time symmetrical figure, and the position where the center of gravity G2 of the regular triangle Po superposes is an intersection of an N-time symmetrical lattice pattern. It is preferable that the M is three and the N is six, like the first embodiment illustrated in FIGS. 2 to 4. Accordingly, a possibility that the non-flat portions 28A form the lattice pattern can be decreased by the positional relationship among the non-flat portions 28A belonging to different unit arrays U.

Further, the diameter D1 of the non-flat portion 28A is preferably 0.25 times or less the distance between the centers of gravity G2. Further, the diameter D1 of the non-flat portion 28A is preferably from 50 nm to 1000 nm, both inclusive, and is more preferably from 100 nm to 500nm, both inclusive. Further, the shortest distance C1 between the centers G1 of the non-flat portions 28A is preferably from 100 nm to 2000 nm, both inclusive, and is more preferably from 200 nm to 1000 nm, both inclusive. Further, an aspect ratio (H1/D1) of the non-flat portion 28A, where the depth of the non-flat portion 28A is H1, is preferably from 0.1 to 10, both inclusive, and is more preferably from 0.5 to 5.0, both inclusive. Note that the dimensions of the non-flat portion 28A are not limited to the above-described examples.

As the material of the photonic crystal 25, an organic material such as a synthetic resin, or an inorganic material such as a metal or a ceramic can be used.

As the synthetic resin, a thermoplastic resin such as polyethylene, polypropylene, polymethylpentene, polycycloolefin, polyamide, polyimide, acryl, polymethacrylic acid ester, polycarbonate, polyacetal, polytetrafluoroethylene, polybutylene terephthalate, polyethylene terephthalate, polyvinyl chloride, polyvinylidene chloride, polystyrene, polyphenylene sulfide, polyether sulfone, or polyetheretherketone, or a thermosetting resin such as a phenol resin, a urea resin, or an epoxy resin, can be used.

As the ceramic, a ceramic such as silica, alumina, zirconia, titania, or yttria can be preferably used.

As the metal, a steel material or various alloys can be used. To be specific, stainless steel, titanium or a titanium alloy can be preferably used.

Among the above-described various materials, a polycycloolefin-based synthetic resin or a silica-based ceramic is more preferable, in light of optical characteristics, processability, tolerance to a solution containing a target substance (a substance to be targeted), absorbability of a target substance capturing material (specific bonding substance), and tolerance to a washing agent. Between the polycycloolefin-based synthetic resin and the silica-based ceramic, the polycycloolefin-based synthetic resin is most preferable because of excellent processability.

The photonic crystal 25 is manufactured by application of fine processing to a surface of a substrate made of the above-described material. As a processing method, laser processing, heat nanoimprint, optical nanoimprint, or a combination of a photo mask and etching can be used. Especially, when the thermoplastic resin such as the polycycloolefin-based synthetic resin is used as the material, a method by the heat nanoimprint is preferable.

Next, the metal film 26 will be explained. In the first embodiment, as illustrated in FIG. 4, the reflection surface 29 of the photonic crystal 25 is coated with the metal film 26. It is preferable to form the metal film 26, using any one or more types of gold (Au), silver (Ag), platinum (Pt), and aluminum (Al). In the first embodiment, the metal film 26 is formed of Au. Au is excellent in stability, and is thus preferable as the reflection surface 29. When any one or more types of silver (Ag) and aluminum (Al) are used as the metal film 26, it is preferable to coat the surface with gold. In doing so, a use amount of gold can be decreased, and a manufacturing cost of the photonic crystal 25 can be suppressed.

Since the metal-film coated photonic crystal 21 is obtained such that the reflection surface 29 of the photonic crystal 25 is coated with the metal film 26, a non-flat portion 28B of the metal-film coated photonic crystal 21 is formed on the reflection surface 29, corresponding to the non-flat portion 28A of the photonic crystal 25. Further, a diameter D2 of the non-flat portion 28B is preferably equal to or less than 0.25 times the minimum distance B1 between centers of gravity G2. Further, although depending on the thickness of the metal film 26, a diameter D2 of the non-flat portion 28B is preferably from 50 nm to 1000 nm, both inclusive, and is more preferably from 100 nm to 500 nm, both inclusive. Further, a shortest distance C2 between the centers G1 of the non-flat portions 28B is preferably from 80 nm to 2400 nm, both inclusive, and is more preferably, from 200 nm to 1000 nm, both inclusive. Further, an aspect ratio (H2/D2) of the non-flat portion 28B where the depth of the non-flat portion 28B is H2 is preferably from 0.1 to 10, both inclusive, and is more preferably from 0.5 to 5.0, both inclusive. Note that the dimensions of the non-flat portion 28B are not limited to the above-described dimensions.

If the film thickness of the metal film 26 is small, a part of incident light on the photonic crystal 25 may transmit the metal film 26. As a result, there is a possibility of a decrease in an amount of information obtained from reflected light, and there is a possibility that the reflected light from the photonic crystal 25 includes a large volume of unnecessary information such as diffracted light or the reflected light from a back surface of the photonic crystal 25. By appropriately making the film thickness of the metal film 26 large, the unnecessary information included in the reflected light from the photonic crystal 25 can be decreased, and detection accuracy of the target substance and measurement accuracy of the concentration can be improved. Further, when the film thickness of the metal film 26 is appropriately small, a detailed pattern shape can be easily manufactured on the surface 27 of the photonic crystal 25, and thus it is preferable. For example, a corner of the pattern becomes sharp, and the dimension of the pattern can be easily secured. Based on the above perspective, the film thickness of the metal film 26 is preferably from 30 nm to 1000 nm, both inclusive, is more preferably from 150 nm to 500 nm, both inclusive, and is still more preferably from 200 nm to 400 nm, both inclusive, in the first embodiment. This is because change of the reflectance to the wavelength becomes nearly similar when the film thickness of the metal film 26 exceeds 200 nm.

The metal film 26 can be formed on the reflection surface 29 of the photonic crystal 25 by means of sputtering, a deposition apparatus, or the like. It is preferable to form an outermost surface of the metal film 26 with Au. When Ag, Pt, or Al is used as the metal film 26, the wavelength of the reflected light in each extreme value becomes 1.5 times that of a case where Au is used as the metal film 26. As described above, sensitivity of Ag, Pt, and Al is 1.5 times that of Au. Since Ag is easily oxidized, it is preferable to form an oxide thin film of Au or $SiO_2$, which is less easily oxidized, after forming Ag on the reflection surface 29 of the photonic crystal 25. In this case, a film of Au having the thickness of 5 nm can be formed on a surface of a film of Ag having the thickness of 200 nm. When the film of Au having the thickness of 5 nm is formed on the film of Ag having the thickness of 200 nm, the sensitivity becomes 1.5 times that of a film of Au having the thickness of 200 nm. Further, no change of the sensitivity is seen between existence and non-existence of the film of Au of 5 nm. Al is also easily oxidized similarly to Ag, and thus it is preferable to form the oxide thin film of Au or $SiO_2$, which is less easily oxidized, after forming a film of Al on the surface 27 of the photonic crystal 25. In a case of Pt, it is also preferable to form the oxide thin film of Au or $SiO_2$ because of modification with an antibody or the like.

Further, it is preferable to reform the reflection surface 29 of the photonic crystal 25, using 3-triethoxysilylpropylamine (APTES) or the like. When the metal film 26 of Au or Ag is formed on the reflection surface 29 of the photonic crystal 25, it is preferable to reform the reflection surface 29 of the photonic crystal 25, using a carbon chain having a thiol group in one end, and a functional group such as an amino group or a carboxyl group in the other end, instead of APTES. When the metal film 26 of other than Au or Ag is formed on the reflection surface 29 of the photonic crystal 25, it is preferable to reform the reflection surface 29 of the photonic crystal 25, using a silane-based coupling agent, for example, APTES, having a functional group in one end.

In the first embodiment, the array of the plurality of non-flat portions 28B arranged on the surface of the metal-film coated photonic crystal 21 includes the plurality of unit arrays U in which three non-flat portions 28B are arranged such that each one center G1 of the non-flat portions 28B superposes a position of a vertex in the regular triangle Po. Further, in the array in which the plurality of non-flat portions 28B is arranged, the plurality of unit arrays U is arranged such that each one center of gravity G2 of the regular triangle Po superposes a position of an intersection of the lattice pattern La, the lattices intersecting with each other at an angle of 60°. Accordingly, the unit arrays U are arranged to form the lattice pattern La. Here, the wavelength, with which the reflected light of the light incident on the reflection surface 29 of the metal-film coated photonic crystal 21 exhibits the extreme value, depends on the cycle of the lattice pattern La of the reflection surface 29. On the reflection surface 29, the cycle of the lattice pattern La is equal to the minimum distance B1 between the centers of gravity G2. Therefore, in the first embodiment, the wavelength, with which the reflected light of the light incident on the reflection surface 29 exhibits the extreme value, depends on the minimum distance B1 between the centers of gravity G2.

Further, the unit array U includes the plurality of non-flat portions 28B. Therefore, the number of the non-flat portions 28B as the entire reflection surface increases, compared with a case where the non-flat portions 28B form the lattice pattern La. Further, the length C1, that is the shortest distance between the centers G1 of the non-flat portions 28B, and also is a length of one side of the regular triangle Po in the unit array U, is preferably from 0.4 times to 0.6 times (both inclusive) the minimum distance B1 between the centers of gravity G2 that is equal to the minimum distance between the intersections of the lattice pattern La.

As a result, on the reflection surface 29, the number of the non-flat portions 28B can be increased without making the cycle of the lattice pattern La small, the cycle being the minimum distance B1 between the centers of gravity G2. Further, on the reflection surface 29, the number of the non-flat portions 28B per unit area increases while the diameter D2 of the non-flat portion 28B is kept to be a desired size. Accordingly, the metal-film coated photonic crystal 21 of the first embodiment can enhance the sensitivity when used as a sensor, by an increase in a specific surface area of the reflection surface 29. Therefore, the sensor using the metal-film coated photonic crystal 21 of the first embodiment can enhance the sensor sensitivity while causing the cycle of the lattice pattern La of the reflection surface 29 to be a desired value.

Further, all of the non-flat portions 28B belong to any of the unit array U. The non-flat portions 28B belonging to one unit array U are different from the non-flat portions 28B belonging to adjacent unit arrays U. Accordingly, the non-flat portion 28B is not arranged in the position G3 of FIG. 3, for example. Here, the position G3 is a position of a center of gravity of a triangle obtained by connecting the centers of gravity G2 of adjacent three regular triangles Po with line segments. In the metal-film coated photonic crystal 21 of the first embodiment, the non-flat portion 28B is not arranged alone. Therefore, the non-flat portion 28B does not form the lattice pattern La. Therefore, on the reflection surface 29, the number of the non-flat portions 28B can be increased without making the cycle of the lattice pattern La small, the cycle being the minimum distance B1 between the centers of gravity G2. Therefore, the sensor using the metal-film coated photonic crystal 21 of the first embodiment can enhance the sensor sensitivity while more reliably causing the cycle to be a desired value.

With such an arrangement of the non-flat portions 28B, the non-flat portions 28B are arranged on the reflection surface 29 to have only a six-time rotational symmetry. Therefore, one large peak appears in the spectrum of the reflected light, and the depth of the peak shape becomes large. As a result, small change on the reflection surface 29 can be highly accurately detected, and a noise in measurement can be decreased. Therefore, the sensor using the metal-film coated photonic crystal 21 of the first embodiment improves the S/N ratio, and enhances the sensor sensitivity, compared with an arrangement including a plurality of rotational symmetries.

Figure 32A:
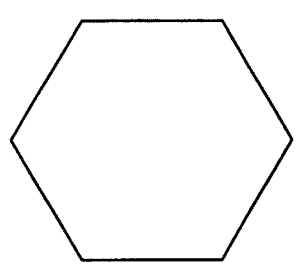
FIGS. 32A and 32B are diagrams illustrating a cross section shape of a non-flat portion along a reflection surface.
Figure 32B:
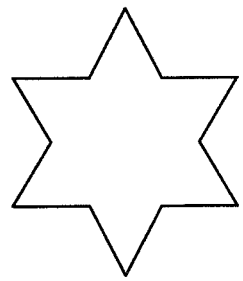

The diameter D2 of the non-flat portion 28B is preferably one time or less the length C1 of one side of the regular triangle Po. If the diameter D2 becomes one time or more the length C1, it is not preferable because adjacent non-flat portions 28B are in contact with each other. Further, a cross section shape of the non-flat portion 28B along the reflection surface 29 is not necessarily a circle, and may be a regular hexagon as illustrated in FIG. 32A or a star as illustrated in FIG. 32B. By causing the non-flat portion 28B to have such a shape, a sharp edge portion is formed on the non-flat portion 28B. As a result, concentration of an electric field is expedited due to an edge effect, and the sensor sensitivity can be further improved. Further, since the shape of the non-flat portion 28B becomes six-time symmetry, in addition to the arrangement of the non-flat portions 28B on the reflection surface 29 is six-time symmetry. Therefore, one clear peak appears in a spectrum of the reflected light, and the sensor sensitivity can be improved. Note that in the cross section shape of the non-flat portion 28B along the reflection surface 29, the circle includes an approximate circle. The approximate circle means a circle having a shape that is deformed compared with a perfect circle, but having deviation from the perfect circle, which falls within a range of a machining error. That is, the approximate circle means a circle that is not the perfect circle but is formed intending to be the perfect circle.

The length of one side of the regular triangle Po is preferably 0.5 times the minimum distance between the intersections of the lattice pattern La, and the one side of the regular triangle Po is preferably parallel with a straight line included in the lattice pattern La. When the non-flat portions 28A are arranged in the direction of the lattice pattern La at regular intervals, the cycle of the lattice pattern La is less likely to be disordered. Therefore, a half-value width of the shape of the spectrum of the reflected light becomes small, and a noise in measurement can be decreased. Therefore, the sensor using the photonic crystal 25 of the first embodiment can improve the S/N ratio, and can enhance the sensor sensitivity.

Figure 5:
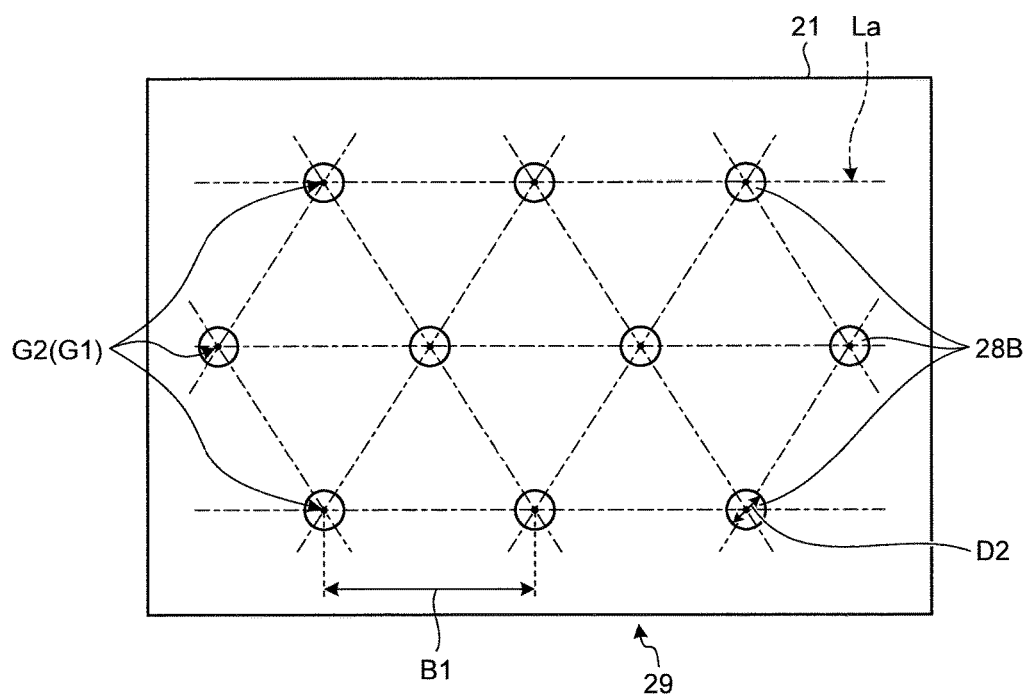
FIG. 5 is a plan view of a metal-film coated photonic crystal of a comparative form.

Next, a comparative form will be explained. FIG. 5 is a plan view of a metal-film coated photonic crystal 21 of a comparative form. In the comparative form, an array, in which a plurality of non-flat portions 28A and 28B is arranged, is arranged such that one center G1 superposes the position of the intersection of the six-time symmetrical lattice pattern La. A distance between the centers G1 in the comparative form is equal to the minimum distance B1 between the centers of gravity G2 in the first embodiment.

Figure 6:
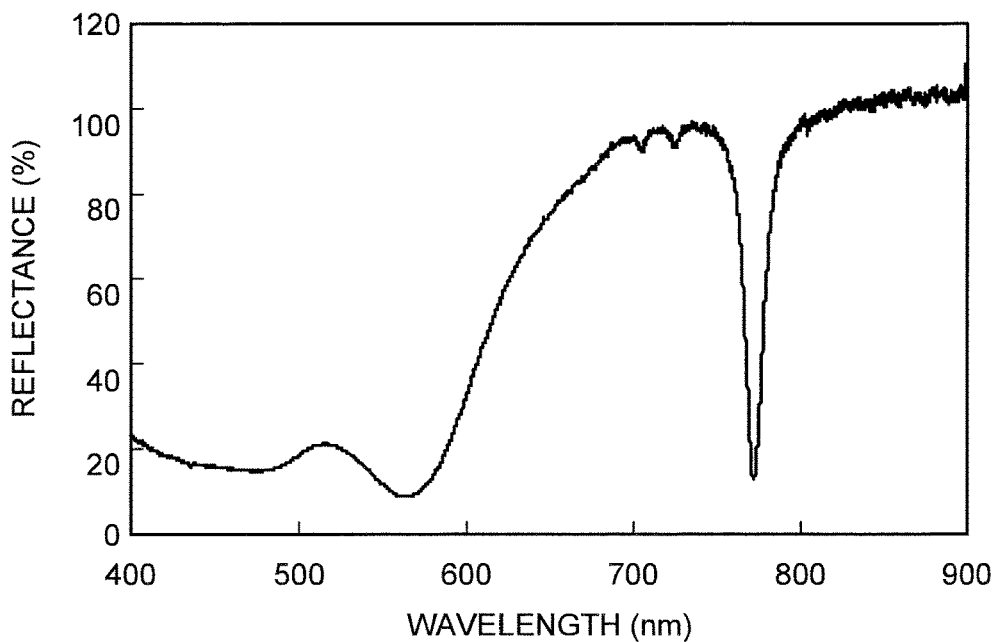
FIG. 6 is a diagram illustrating reflectance with respect to a wavelength of reflected light of an example.
Figure 7:
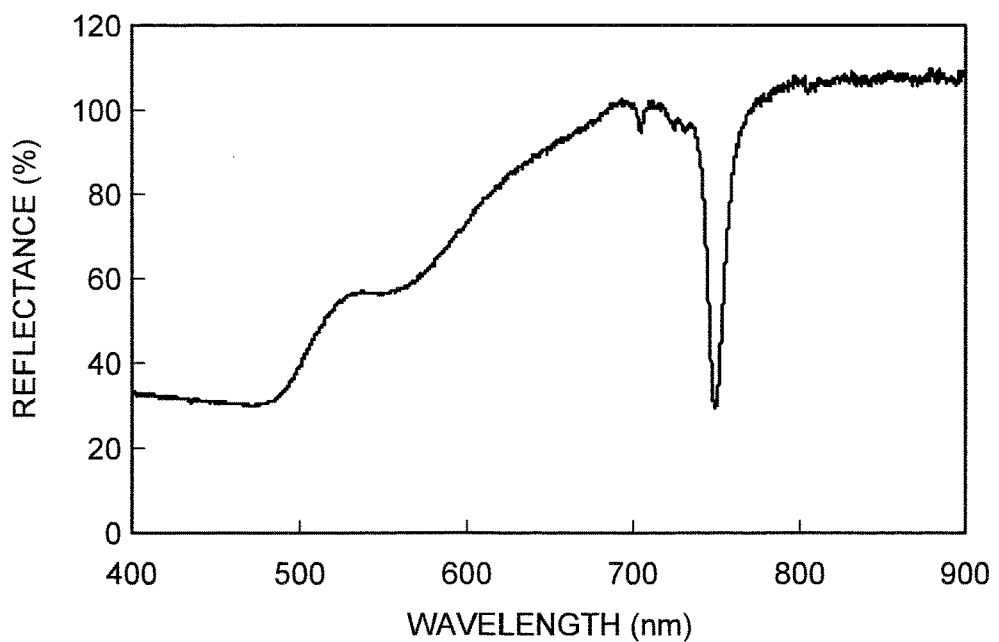
FIG. 7 is a diagram illustrating reflectance with respect to a wavelength of reflected light of a comparative example.

A result of measurement of the wavelength spectrum using the metal-film coated photonic crystal 21 of the first embodiment illustrated in FIGS. 2 to 4 is employed as an embodied example. Further, a result of measurement of a wavelength spectrum using the metal-film coated photonic crystal 21 of the comparative form illustrated in FIG. 5 is a comparative example. The embodied example and the comparative example are results of when the diameter D2 of the non-flat portion 28B is 200 nm, and the minimum distance B1 between the centers of gravity G2 is 600 nm. FIG. 6 is a diagram illustrating reflectance with respect to the wavelength of the reflected light of the embodied example. FIG. 7 is a diagram illustrating reflectance with respect to a wavelength of reflected light of the comparative example. FIGS. 6 and 7, indicate that the embodied example and the comparative example show the wavelengths with which the reflectance exhibits an extreme value, due to the minimum distance B1 between the centers of gravity G2 being 600 nm.

Figure 8:
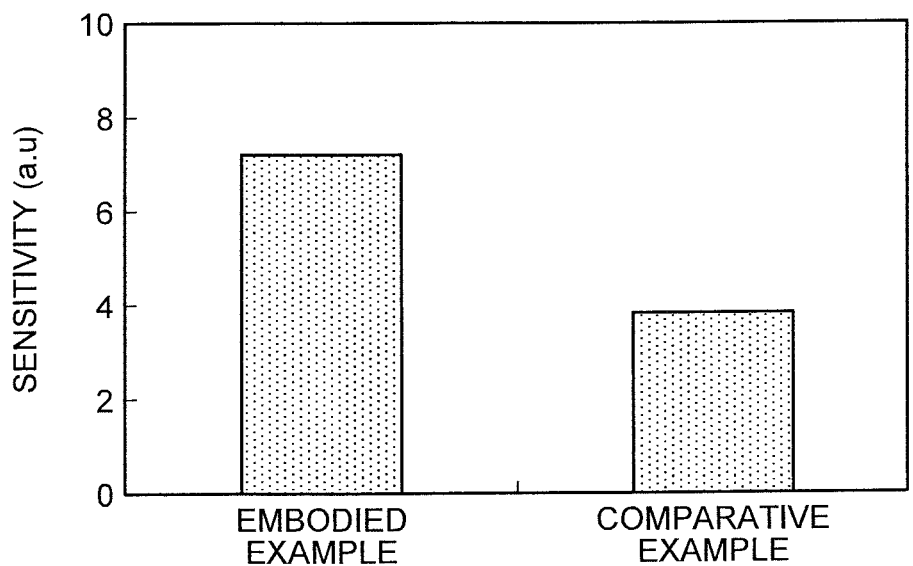
FIG. 8 is a diagram illustrating sensitivity of a sensor of an example and a comparative example.

FIG. 8 is a diagram illustrating sensitivity as a sensor in the embodied example and in the comparative example. FIG. 8 illustrates sensitivity of a sensor, the sensitivity being obtained from a shift amount of a wavelength having the extreme value, of when biotin is fixed to the surface 27 of the reflection surface 29, and 100 nMol/L of avidin is brought to react with biotin, of the embodied example and the comparative example. From FIG. 8, it is found that the embodied example has higher sensitivity as a sensor than the comparative example. This is because the number of the non-flat portions 28A and 28B per unit area increases in the embodied example, compared with the comparative example, even if the cycle of the lattice pattern La on the reflection surface 29 is the same, which is the minimum distance B1 between the centers of gravity G2.

Figure 9:
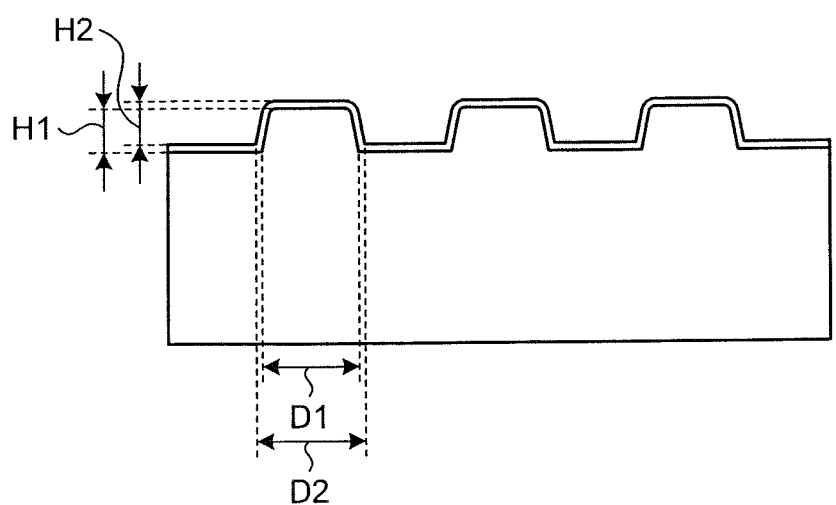
FIG. 9 is a diagram illustrating an A-A cross section in FIG. 3 of when a non-flat portion is a protruding portion.

Note that, in the above description, the non-flat portion according to the first embodiment is the recessed portion as illustrated in FIG. 4. However, the non-flat portion may be the protruding portion as illustrated in FIG. 9. The non-flat portions 28A and 28B are columnar protruding portions protruding from the surface 27. FIG. 9 is a diagram illustrating an A-A cross section in FIG. 3 of a case where the non-flat portion is the protruding portion.

(Method of Manufacturing Photonic Crystal)

Figure 10:
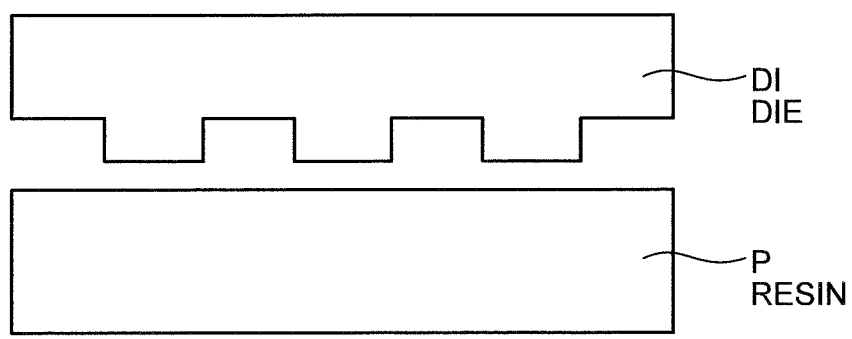
FIG. 10 is a diagram for describing a method of manufacturing a photonic crystal.
Figure 11:
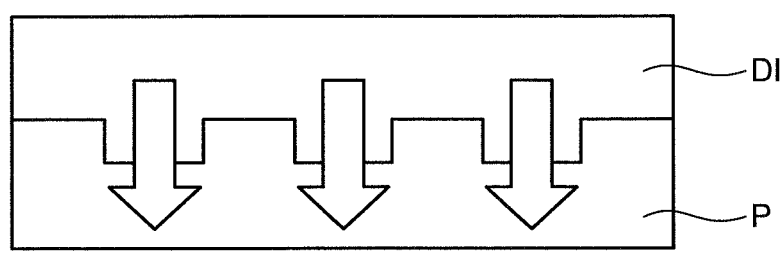
FIG. 11 is a diagram for describing a method of manufacturing a photonic crystal.
Figure 12:
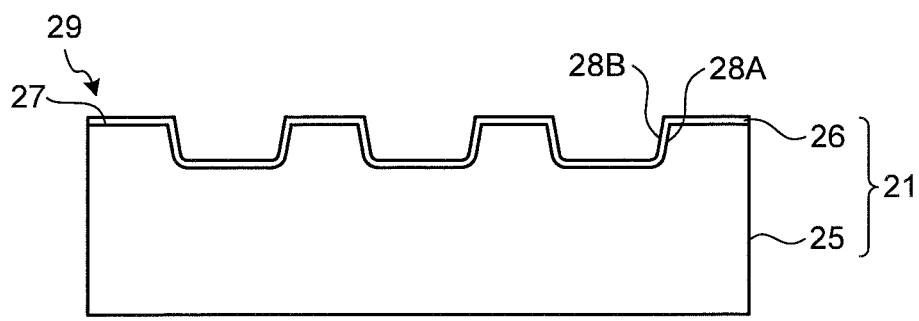
FIG. 12 is a diagram for describing a method of manufacturing a photonic crystal.

Next, an example of a process of manufacturing the metal-film coated photonic crystal 21 by heat nanoimprint will be explained. FIGS. 10 to 12 are diagrams for explaining a method of manufacturing a photonic crystal. As illustrated in FIG. 10, in the heat nanoimprint, a die DI having a nano-level microstructure, or a pattern of a nano-level cyclic structure is used. Then, as illustrated in FIG. 11, the heated die DI is pressed against a sheet resin P and is pressed with predetermined pressure for a predetermined time. When a surface temperature of the die DI becomes a predetermined temperature, the die is released, and the microstructure or the cyclic structure is transferred to the sheet resin P. Accordingly, the photonic crystal 25 can be obtained.

When the resin P is a cycloolefin-based polymer, the die DI is heated to about 160° C. and is pressed with pressure of about 12 MPa for a predetermined time. It is preferable to release the die when the surface temperature of the die DI becomes about 60° C.

After the photonic crystal 25 is manufactured, the metal film 26 is formed on a surface, which has been in contact with the die DI, by means of sputtering or a deposition apparatus, as illustrated in FIG. 12, and then the metal-film coated photonic crystal 21 is completed.

(Target Substance Capturing Material)

Next, the target substance capturing material that captures the target substance will be explained. The target substance is an object to be detected by the target substance detecting device 10, and may be any of a macromolecule such as a protein, an oligomer, or a low molecule. The target substance is not limited to a single molecule, and may be a complex made of a plurality of molecules. Examples of the target substance include a pollutant in the atmosphere, a toxic substance in water, and a biomarker in a human body. Among them, cortisol is preferable. Cortisol is a low-molecular substance having a molecular weight of 362 g/mol. The cortisol concentration in saliva increases when a human feels stress. Therefore, cortisol attracts attention as a substance with which the degree of stress felt by the human is evaluated. When the cortisol concentration contained in saliva of a human is measured using the cortisol as the target substance, the degree of stress can be evaluated. When the degree of stress is evaluated, whether a person to be measured is in a level of stress state leading to a mental disease such as depression can be determined.

The target substance capturing material is a substance bonded with the target substance and capturing the target substance. Here, the bonding may be non-chemical bonding, such as bonding by physisorption or Van der Waals force, in addition to the chemical bonding. Preferably, the target substance capturing material specifically reacts with the target substance, and captures the target substance, and is preferable to be an antibody having the target substance as an antigen. The specific reaction means selective bonding with the target substance in a reversible or irreversible manner to form a complex, and is not limited to a chemical reaction. Further, a substance to specifically react with the target substance capturing material may exist other than the target substance. Even if there is a substance to react with the target substance capturing material in a sample, other than the target substance, the target substance can be quantified when affinity of the substance is extremely smaller than that of the target substance. As the target substance capturing material, an antibody having the target substance as an antigen, an artificially manufactured antibody, a molecule constituted from a substance that composes DNA such as adenine, thymine, guanine and cytosine, and a peptide, or the like can be used. When the target substance is cortisol, the target substance capturing material is preferably a cortisol antibody.

To manufacture the target substance capturing material, a known method can be employed. For example, the antibody can be manufactured by a serum test, a hybridoma method, or a phage display method. The molecule constituted from a substance that composes DNA can be manufactured by systematic evolution of ligands by exponential enrichment (SELEX method), for example. The peptide can be manufactured by a phage display method, for example. The target substance capturing material is not necessarily labeled with some sort of enzyme or isotope. However, the target substance capturing material may be labeled with enzyme or isotope.

In the first embodiment, the target substance capturing material is fixed to the reflection surface 29 of the metal-film coated photonic crystal 21 illustrated in FIG. 4. Examples of means for fixing the target substance capturing material to the reflection surface 29 of the metal-film coated photonic crystal 21 include chemical bond and physical bond methods such as covalent bond, chemisorption, and physisorption. These means can be appropriately selected according to a nature of the target substance capturing material. For example, when absorption is selected as the fixing means, an operation of the absorption is as follows. For example, a solution containing the target substance capturing material is dropped on the reflection surface 29 of the metal-film coated photonic crystal 21. The target substance capturing material is absorbed by the reflection surface 29 while the metal-film coated photonic crystal 21 is kept in a room temperature for a predetermined time, or is cooled/heated for a predetermined time, as needed.

The photonic crystal biosensor 11 allows an antibody (for example, a cortisol antibody), which is bonded only with a specific antigen (for example, cortisol), to be absorbed by (fixed to) the surface of the reflection surface 29 of the metal-film coated photonic crystal 21 in advance. Accordingly, the photonic crystal biosensor 11 can detect the specific antigen. This uses optical characteristics of the photonic crystal 25, and various biological reactions/chemical reactions occurring on the surface or in the vicinity of the surface of the photonic crystal 25, for example, an antigen antibody reaction in which the specific antigen reacts only with the specific antibody.

The photonic crystal biosensor 11 may be obtained such that a blocking agent (protecting substance) is fixed on the reflection surface 29 to which the antibody as the target substance capturing material is fixed. The blocking agent is fixed before the target substance is brought to come in contact with the photonic crystal biosensor 11. The reflection surface 29 of the photonic crystal 25 is typically superhydrophobic. Therefore, impurities other than the antibody as the target substance capturing material may be absorbed by the reflection surface 29 due to hydrophobic interaction. In addition, the optical characteristics of the photonic crystal 25 are substantially influenced by the surface state. Therefore, it is preferable that the impurities are not absorbed by the reflection surface 29 of the photonic crystal 25. The fixation of the blocking agent to the reflection surface 29 of the photonic crystal 25 improves the detection accuracy of the reflected light.

Therefore, it is preferable to fix the blocking agent in advance so that the impurities and the like are not fixed to a portion other than the portion where the antibody as the target substance capturing material is absorbed by (fixed to) the reflection surface 29 of the photonic crystal 25. To absorb the blocking agent in advance, the blocking agent is brought to come in contact with the surface of the photonic crystal 25. As the blocking agent, skim milk, bovine serum albumin (BSA), or the like can be used.

Next, a basic principle in which the photonic crystal biosensor 11 detects an antibody as a target substance and the concentration thereof will be explained. FIGS. 13 to 16 are diagrams for describing a principle of the photonic crystal biosensor 11. Typically, the photonic crystal biosensor 11 detects a small amount of a protein or a low-molecular substance, using various optical characteristics of the photonic crystal 25, and biological reaction/chemical reaction occurring on the surface or in the vicinity of the surface of the photonic crystal 25, for example, an antigen/antibody reaction in which a specific antigen reacts only with a specific antibody. The photonic crystal biosensor 11 then uses a surface plasmon resonance phenomenon when the reflection surface 29 of the metal-film coated photonic crystal 21 is irradiated with light having a specific wavelength and/or a phenomenon in which the extreme value of the wavelength of the reflected light is shifted due to a local surface plasmon resonance phenomenon.

Figure 13:
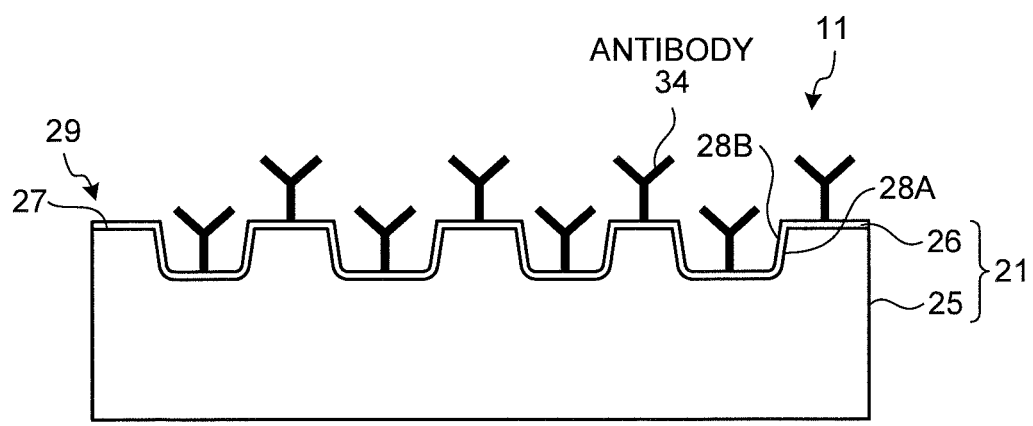
FIG. 13 is a diagram for describing a principle of a photonic crystal biosensor.

As illustrated in FIG. 13, an antibody (target substance capturing material) 34 is fixed to the surface of the reflection surface 29 of the metal-film coated photonic crystal 21 by absorption.

Figure 14:
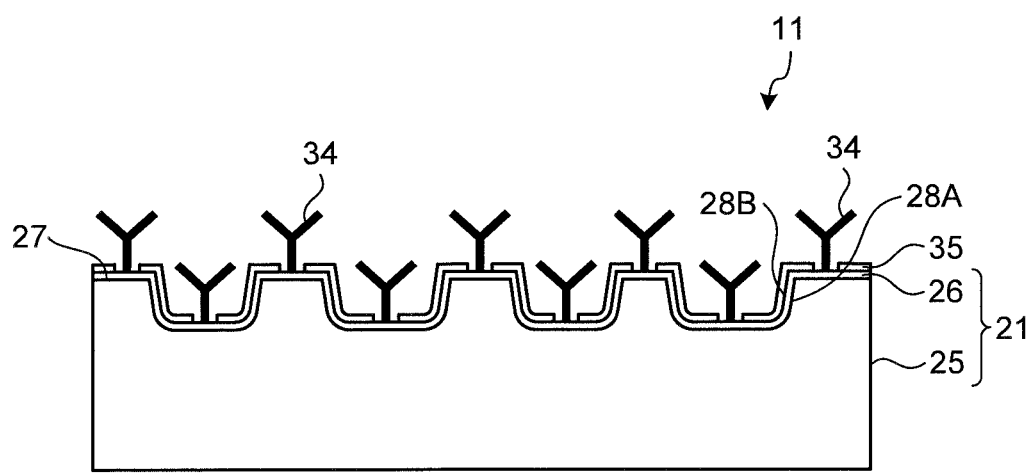
FIG. 14 is a diagram for describing a principle of a photonic crystal biosensor.

Next, as illustrated in FIG. 14, a blocking agent (protecting substance) 35 is absorbed in advance by a portion of the reflection surface 29 other than the portion where the antibody 34 is absorbed, that is, the reflection surface 29 other than the portion where the antibody 34 is absorbed. Accordingly, the impurities and the like are not absorbed by the portion other than the portion of the reflection surface 29 where the antibody 34 is absorbed.

Figure 15:
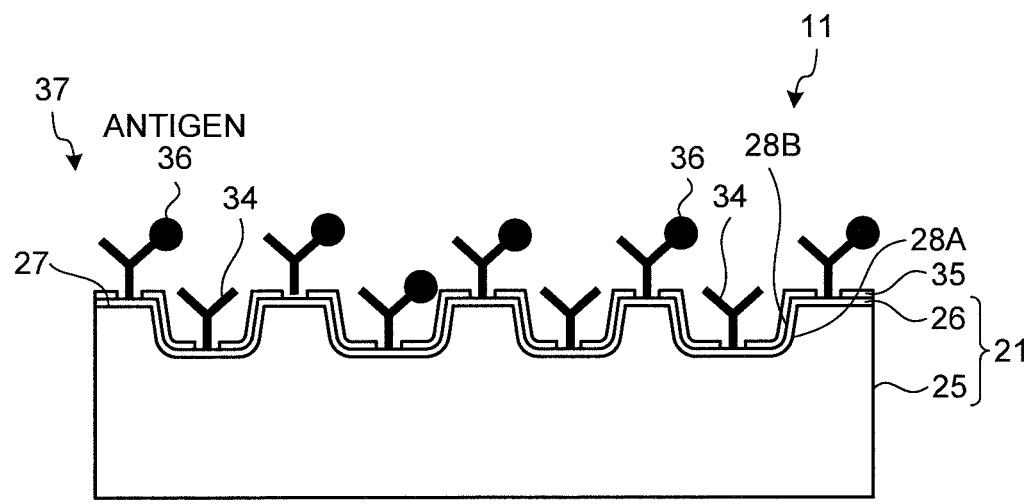
FIG. 15 is a diagram for describing a principle of a photonic crystal biosensor.

Next, as illustrated in FIG. 15, an antigen (target substance) 36 is brought to come in contact with the photonic crystal biosensor 11 in which the antibody 34 and the blocking agent 35 are absorbed, and an antigen antibody reaction is performed. A complex 37 in which the antigen 36 is captured by the antibody 34 is fixed to the reflection surface 29.

Figure 16:
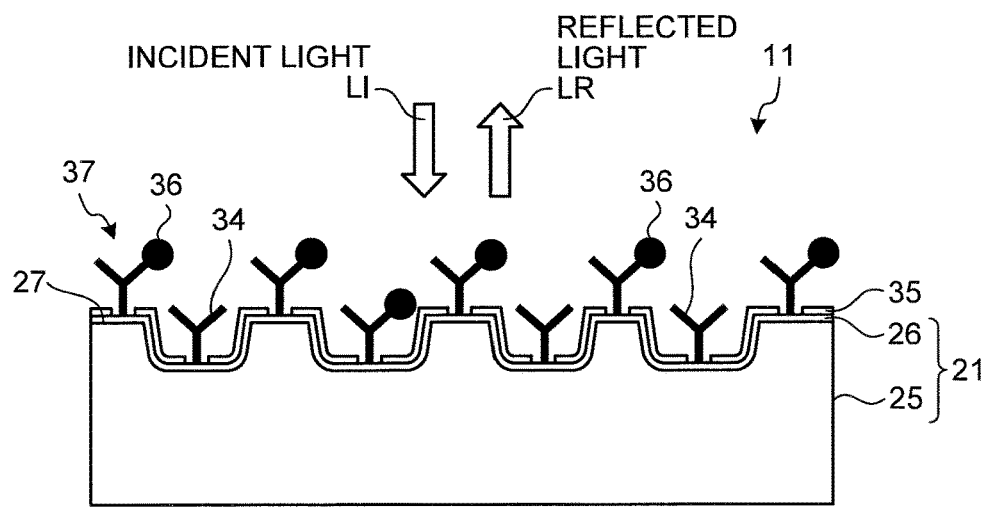
FIG. 16 is a diagram for describing a principle of a photonic crystal biosensor.

Next, the photo-detection section 12 illustrated in FIG. 1 irradiates the reflection surface 29 of the metal-film coated photonic crystal 21 with light (incident light) LI having a specific wavelength, in parallel light, in a state where the antigen 36 is captured on the reflection surface 29 of the photonic crystal 25, as illustrated in FIG. 16. Then, the photo-detection section 12 illustrated in FIG. 1 detects reflected light LR reflected on the reflection surface 29, and obtains the wavelength of the extreme value of the reflected light LR. Then, the processing unit 13 illustrated in FIG. 1 obtains the wavelength in the extreme value of the intensity of the reflected light LR and the shift amount of the wavelength in the extreme value of the intensity, and detects existence/non-existence of the antigen 36 captured on the reflection surface 29 of the metal-film coated photonic crystal 21, or obtains the concentration of the antigen 36.

The photonic crystal biosensor 11 can change various types of biological substances such as a protein, or a type of a low-molecular weight substance, which is the substance to be detected, by changing a type of a combination of the antibody 34 and the antigen 36, based on the above-described principle.

In the photonic crystal biosensor 11, when the antigen 36 is captured by the antibody 34 fixed to the reflection surface 29, the state of the reflection surface 29 is changed, and the reflected light LR is changed. The photonic crystal biosensor 11 outputs an optical physical amount. The physical amount correlates with the change of the surface state in the reflection surface 29 of the metal-film coated photonic crystal 21, and correlates with the amount of the complex 37 that is formed such that the antigen 36 is captured by the antibody 34 fixed to the reflection surface 29. The optical physical amount is, for example, the shift amount of the wavelength with which the intensity of the reflected light LR becomes the extreme value, the change amount of the reflectance of light, the shift amount of the wavelength with which the reflectance of light becomes the extreme value, the intensity of the reflected light LR, the amount of change of the extreme value of the intensity of the reflected light LR, and the like. In the first embodiment, the intensity of the reflected light LR, or the shift amount of the wavelength with which the reflectance of light becomes the extreme value is used.

To output the optical physical amount, the following processes are performed, for example. Light is vertically incident on the reflection surface 29 of the metal-film coated photonic crystal 21, and the reflected light LR is detected. The light can be incident on the reflection surface 29 of the metal-film coated photonic crystal 21 with an angle with respect to a perpendicular line of the reflection surface 29, and the reflected light LR can be detected. By detection of the reflected light LR, the target substance detecting device 10 illustrated in FIG. 1 can be made compact. When vertically incident and vertically reflected light is detected, it is preferable to cause the light to be incident, using a bifurcated optical fiber, to detect the reflected light LR. This structure will be described below.

(Method of Manufacturing Photonic Crystal Biosensor)

Figure 17:
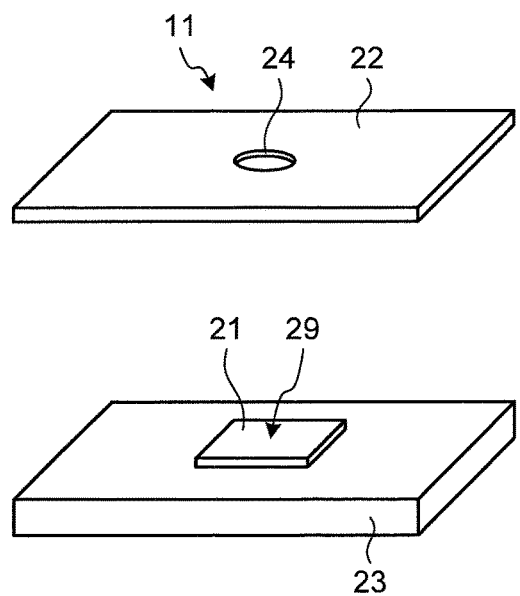
FIG. 17 is a diagram for describing a photonic crystal biosensor.
Figure 18:
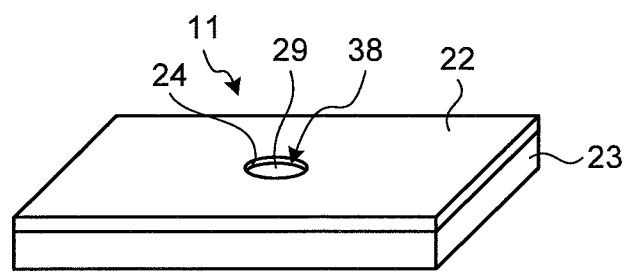
FIG. 18 is a diagram for describing a photonic crystal biosensor.
Figure 19:
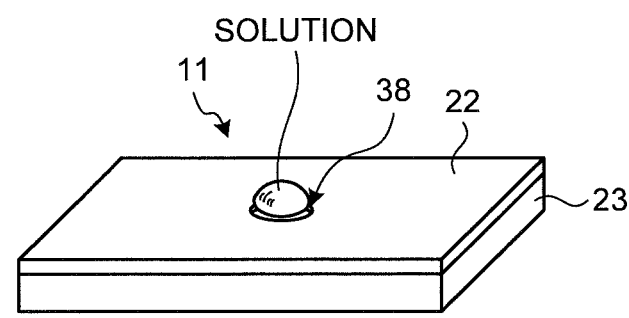
FIG. 19 is a diagram for describing a photonic crystal biosensor.

Next, an example of manufacturing the photonic crystal biosensor 11 illustrated in FIG. 1 will be explained. FIGS. 17 to 19 are explanatory diagrams of the photonic crystal biosensor 11. As illustrated in FIG. 17, the photonic crystal biosensor 11 is manufactured such that the metal-film coated photonic crystal 21 is installed on the lower plate 23, then as illustrated in FIG. 18, the upper plate 22 is installed on the lower plate 23, and the metal-film coated photonic crystal 21 is sandwiched by the lower plate 23 and the upper plate 22. An end portion of the opening 24 at the lower plate 23 side is blocked by the reflection surface 29 of the photonic crystal 25. With such a structure, the upper plate 22 includes a fixed volume of liquid drop holding portion 38 formed by being surrounded by an inner wall of an opening 24 side and the reflection surface 29. The inner wall of an opening 24 side refers to an inner wall of the upper plate 22, which is a boundary surface between the upper plate 22 and the opening 24.

FIG. 19 illustrates a state in which a predetermined solution is dropped in the liquid drop holding portion 38. In this case, the liquid drop holding portion 38 exerts a liquid drop holding function, and thus suppresses the solution from flowing out of the opening 24. Further, as the amount of the solution, an amount as much as being filled in the liquid drop holding portion 38 will be sufficient to detect and/or measure the target substance.

The shape of the opening 24 is not limited to the columnar shape, and may be another shape as long as the opening 24 can hold the liquid droplet inside the opening 24. Further, when the opening 24 is a columnar shape, the diameter can be various diameters in accordance with a type of a combination of the antibody 34 and the antigen 36, necessary measurement accuracy, or an optical system of a detector of the reflected light. The diameter of the opening 24 is preferably from 0.5 mm to 10 mm, both inclusive, and is more preferably from 2 mm to 6 mm, both inclusive, in consideration of an operation of when the antigen 36 is absorbed by the antibody 34, convenience of handling, and the like.

Materials of the upper plate 22 and the lower plate 23 are not especially limited. However, it is preferable to use stainless steel, a poly cycloolefin-based resin, or silica, in light of cleanliness of the surfaces of the upper plate 22 and the lower plate 23.

Next, another form of the photonic crystal biosensor 11 will be explained. The upper plate 22 may be formed of a hydrophobic material. Especially, when a so-called hydrophilic solution such as saliva is detected/measured, when the upper plate 22 is formed of a hydrophobic material, the solution can be reliably collected in the liquid drop holding portion 38. Further, when a lipophilic solution such as a lipid is detected/measured, when the upper plate 22 is formed of a hydrophobic material, the solution can be reliably collected in the liquid drop holding portion 38.

Further, the upper plate 22 may be formed of a water repellent, oil repellent, or water and oil repellent material. Further, surface treatment or coating that exerts hydrophobicity, hydrophilicity, water repellence, or oil repellence may be applied to the upper plate 22. In doing so, the solution can be reliably collected to the liquid drop holding portion 38.

In the photonic crystal biosensor 11, it is preferable to mount a fixing material (target-substance capturing portion fixing means or photonic crystal biosensor fixing means) to a lower portion of the photonic crystal biosensor 11. The fixing material positions the photonic crystal biosensor 11 with respect to the photo-detection section 12 illustrated in FIG. 1 and fixes the photonic crystal biosensor 11. As the fixing material, a magnet sheet, a double-sided tape, an adhesive, or the like can be used. Further, to fix the photonic crystal biosensor 11, a vacuum chuck or an electrostatic chuck may be used as a fixing mechanism, instead of the fixing material. By fixing the photonic crystal biosensor 11, deviation of a measuring position due to vibration at the time of detection/measurement can be decreased. As a result, more accurate detection/measurement can be performed.

Figure 20:
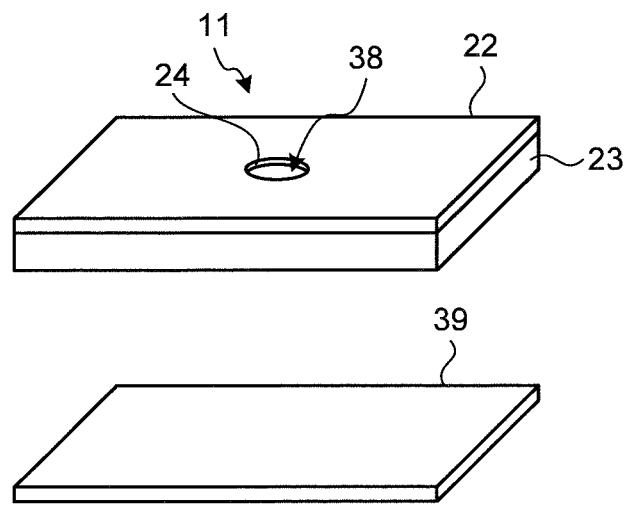
FIG. 20 is a diagram for describing photonic crystal biosensor fixing means.
Figure 21:
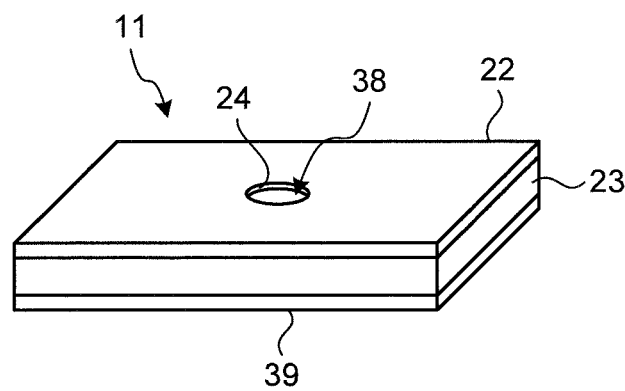
FIG. 21 is a diagram for describing photonic crystal biosensor fixing means.

FIGS. 20 and 21 are diagrams for describing photonic crystal biosensor fixing means. FIG. 20 illustrates a state before a magnet sheet 39 is attached, and FIG. 21 illustrates a state after the magnet sheet 39 is attached. In the photonic crystal biosensor 11, the magnet sheet 39 is attached to a side in the lower portion of the photonic crystal biosensor 11. The magnet sheet 39 functions as the photonic crystal biosensor fixing means.

The photonic crystal biosensor 11 is uniformly manufactured by heat nanoimprint or the like. To cause the target substance detecting device 10 to be able to more accurately detect the reflected light, it is preferable to accurately position an incident part and a reflection part of the light irradiated the photonic crystal biosensor 11.

That is, it is preferable that a positional relationship between the photonic crystal biosensor 11 and a measuring probe described below at the time of measurement is the same before and after the antigen antibody reaction, and it is preferable to measure the same portion. Therefore, it is preferable that the distance between the measuring probe and the reflection surface 29 of the photonic crystal biosensor 11 is the same before and after the antigen antibody reaction, and it is preferable to fix the distance from 50 μm to 500 μm. As the photonic crystal biosensor 11 includes the upper plate 22, the upper plate 22 functions as a spacer, and can cause the distance between the measuring probe and the reflection surface 29 of the photonic crystal biosensor 11 to be constant.

Further, the photonic crystal biosensor 11 may be marked with a positioning marker that displays a specific position on the reflection surface 29. The marker may be provided by photolithography, sputtering, deposition, or a liftoff process using the aforementioned methods, printing with an ink, pattern formation by imprint, or the like. The marker may be attached to either a surface (the reflection surface 29 side) or a back surface (an opposite side to the reflection surface 29) of the photonic crystal biosensor 11 as long as the position of the marker can be read. Further, the marker may be attached to the photonic crystal 25 itself, avoiding a measuring portion of the photonic crystal 25. Further, the marker may be attached to the upper plate 22 and the lower plate 23.

Figure 22:
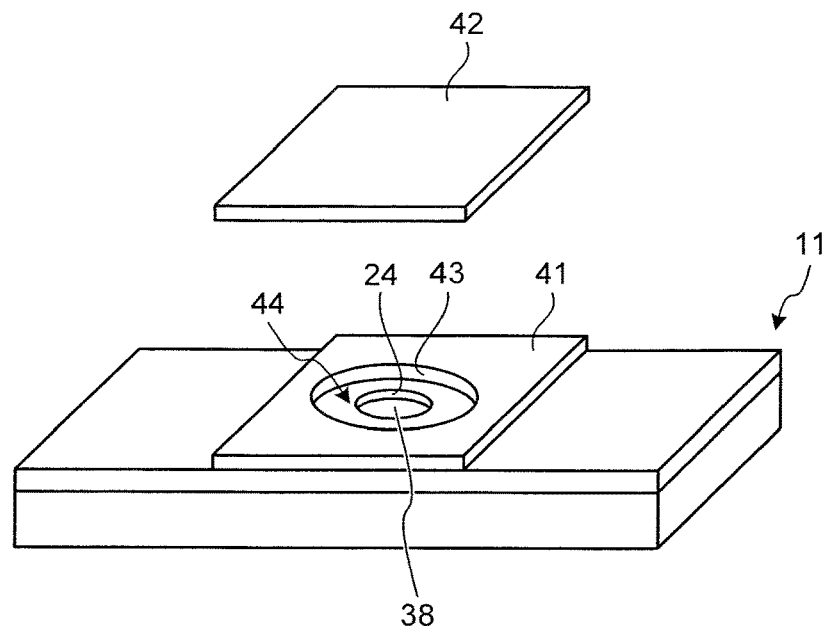
FIG. 22 is a diagram for describing another form of a photonic crystal biosensor.

Next, still another form of the photonic crystal biosensor 11 will be explained. FIG. 22 is a diagram for describing another form of the photonic crystal biosensor 11. As illustrated in FIG. 22, the photonic crystal biosensor 11 includes a member that blocks the opening 24. The member that blocks the opening 24 includes a cover with a hole 41, hereinafter, hole-opened cover 41, and a sheet 42. The hole-opened cover 41 is a plate member including an opening 43, and is provided on the surface (reflection surface 29 side) of the photonic crystal biosensor 11. The sheet 42 is provided on a side of the hole-opened cover 41, the side opposite (incident side of light) to the photonic crystal biosensor 11. The sheet 42 functions as a covering member. The openings 24 and 43 of the photonic crystal biosensor 11 are blocked with the hole-opened cover 41 and the sheet 42.

A space surrounded by an inner wall of the hole-opened cover 41 facing the opening 43, the inner wall facing the opening 24, and the reflection surface 29 of the photonic crystal 25 define the fixed volume of liquid drop holding portion 44. The inner wall facing the opening 43 refers to an inner wall of the hole-opened cover 41, that is a boundary surface between the hole-opened cover 41 and the opening 43. The opening 43 is covered with the sheet 42 after the target substance is arranged in the liquid drop holding portion 44. Accordingly, the liquid drop holding portion 44 is blocked by the sheet 42.

By including the hole-opened cover 41 and the sheet 42, the photonic crystal biosensor 11 can suppress evaporation of the solution dropped in the opening 24 of the photonic crystal biosensor 11. Therefore, the photonic crystal biosensor 11 can suppress change of the concentration of the solution due to the evaporation at the time of an antigen antibody reaction. Further, by including the hole-opened cover 41 and the sheet 42, the photonic crystal biosensor 11 can prevent impurities from being mixed to the solution from an outside.

Further, by filling the solution to the liquid drop holding portion 44, it is possible to more accurately measure the reflected light in a state where the solution is filled. In this case, the sheet 42 is preferably a transparent material, and is more preferably a material having less absorption of the light of a wavelength in an extreme value of the intensity of the reflected light. For example, as the material of the sheet 42, quartz (silica) is preferable when measurement is performed with reflected light in from a visible ray region to an ultraviolet ray region.

(Photo-detection Section 12)

Next, the photo-detection section 12 illustrated in FIG. 1 will be explained. The photo-detection section 12 illustrated in FIG. 1 includes a light source 51, a measuring probe 52, a photo-detection device 53, a first optical fiber 54, a second optical fiber 55, and a collimating lens 56. The light source 51 and the measuring probe 52 are optically connected by the first optical fiber 54. The measuring probe 52 and the photo-detection device 53 are optically connected by the second optical fiber 55. A control device connected with the light source 51, the photo-detection device 53, and the like, and which controls the light source 51 and processes a signal from the photo-detection device 53 may be provided, as needed.

Figure 23:
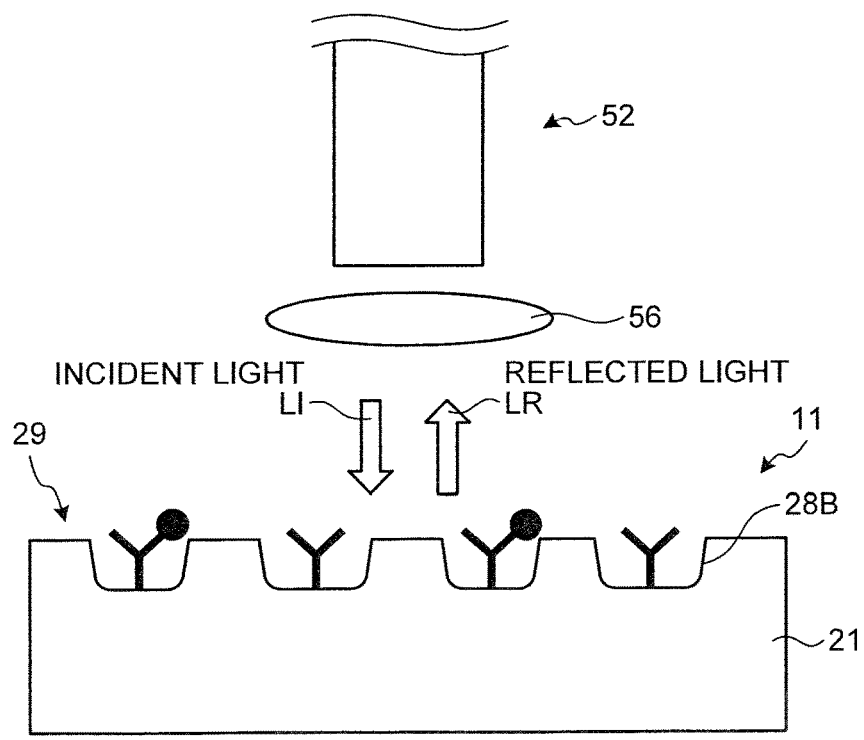
FIG. 23 is a diagram illustrating an example in which a photo-detection section of a target substance detecting device irradiates a photonic crystal biosensor with light.

FIG. 23 is a diagram illustrating an example in which the photo-detection section 12 irradiates the photonic crystal biosensor 11 with light. The first optical fiber 54 illustrated in FIG. 1 guides the light from the light source 51 illustrated in FIG. 1 to the measuring probe 52, and the measuring probe 52 irradiates the reflection surface 29 of the metal-film coated photonic crystal 21 included in the photonic crystal biosensor 11. The collimating lens 56 causes the light emitted from the first optical fiber 54 and irradiated from the measuring probe 52 to be parallel light, and irradiates the reflection surface 29 of the photonic crystal 25 with the parallel light as incident light LI. The second optical fiber 55 receives the light reflected on the reflection surface 29 of the metal-film coated photonic crystal 21, as the reflected light LR, and guides the reflected light LR to the photo-detection device 53 illustrated in FIG. 1. The type of the collimating lens 56 is not especially limited. However, for example, an antireflection film having a nanostructure can be used. The photo-detection device 53 is a device for detecting light, including a light receiving element such as a phototransistor or a charge coupled device (CCD).

Figure 24:
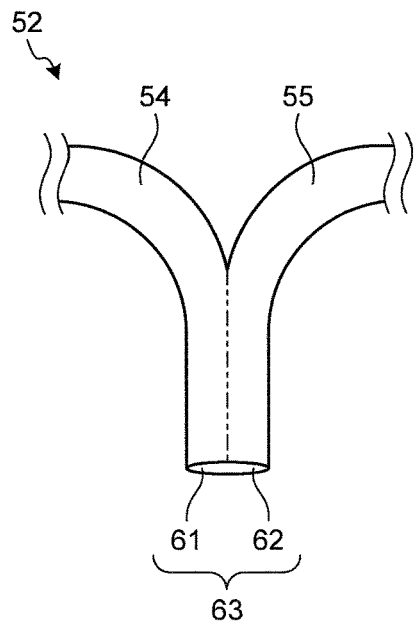
FIG. 24 is a diagram illustrating a structure of a measuring probe included in a photo-detection section of a target substance detecting device.

FIG. 24 is a diagram illustrating a structure of the measuring probe 52 included in the photo-detection section 12 illustrated in FIG. 1. In the measuring probe 52, the first optical fiber 54 and the second optical fiber 55 are joined. In the measuring probe 52, an emission surface 61 of the light of the first optical fiber 54 and an incident surface 62 of the reflected light LR of the second optical fiber 55 are arranged on the same surface (incident/emission surface) 63. As described above, in the measuring probe 52, the first optical fiber 54 and the second optical fiber 55 are integrated at an emission side (an emission surface 61 side) of the first optical fiber 54 and an incident side (an incident surface 62 side) of the second optical fiber 55. The measuring probe 52 allows the light to be incident and detects the reflected light LR, using the first optical fiber 54 and the second optical fiber 55.

Since the measuring probe 52 has such a structure, the measuring probe 52 can allow the incident light LI to irradiate the reflection surface 29 of the photonic crystal 25 to be incident on, and to emit the reflected light LR from the reflection surface 29 from, an approximately the same position. The measuring probe 52 is caused to have the above-described structure, and the light from the measuring probe 52 is caused to be the parallel light, using the collimating lens 56, so that the photo-detection section 12 can allow the incident light LI of the parallel light to be vertically incident on the reflection surface 29. Further, the photo-detection section 12 can receive the reflected light LR vertically reflected on the reflection surface 29. In doing so, the measuring probe 52 can minimize a decrease in the reflected light intensity, and can mainly detect 0-order light component of the reflected light LR. As a result, the processing unit 13 can obtain accurate information of the reflection surface 29 of the metal-film coated photonic crystal 21. Therefore, the detection accuracy of the target substance and the measurement accuracy of the concentration are improved. Note that a technique of detecting the reflected light LR is not limited to the above-described measuring probe 52. For example, a half mirror is arranged between the collimating lens 56 and the reflection surface 29, and the reflected light LR is divided by the half mirror, so that the light may be guided from the second optical fiber 55 to the photo-detection device 53.

Figure 25:
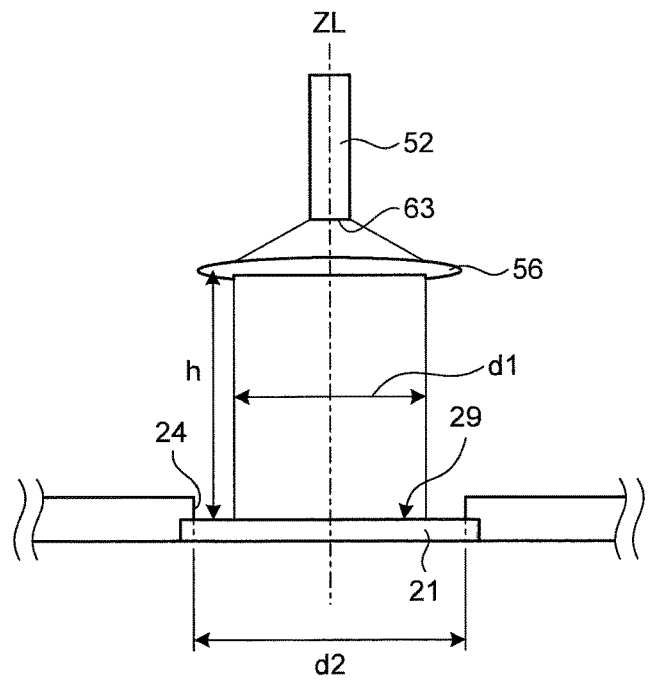
FIG. 25 is a diagram illustrating an evaluation condition of a photo-detection section of a target substance detecting device.

Next, an evaluation condition of the photo-detection section 12 will be explained. FIG. 25 is a diagram illustrating an evaluation condition of the photo-detection section 12 of the target substance detecting device 10 according to the first embodiment. As illustrated in FIG. 25, in the photo-detection section 12, the collimating lens 56 is arranged between the incident/emission surface 63 of the measuring probe 52 and the reflection surface 29 of the metal-film coated photonic crystal 21. A distance (measurement distance) between the collimating lens 56 and the reflection surface 29 is h, a diameter of the parallel light on the reflection surface 29, the parallel light being emitted through the collimating lens 56, is d1, and a diameter of an opening 24 where the reflection surface 29 of the photonic crystal 25 is exposed is d2. In the present evaluation, h is 15 mm or 40 mm, d1 is 3.5 mm, and d2 is 5 mm. Both of an optical axis ZL of the light irradiating the reflection surface 29 and an optical axis ZL of the reflected light reflected at the reflection surface 29 are perpendicular to the reflection surface 29. A diameter of the measuring probe 52 is 200 μm. Irradiated light is white light. Reflectance is a ratio to reflected light intensity of a standard substance (aluminum plate).

(Processing Unit 13)

Next, the processing unit 13 illustrated in FIG. 1 will be explained. The processing unit 13 obtains a wavelength of an extreme value of the reflected light detected by the photo-detection section 12. The processing unit 13 detects existence/non-existence of at least the target substance (antigen 36 illustrated in FIGS. 15 and 16, for example), based on shifting (a wavelength shift amount) of the obtained wavelength of an extreme value. The processing unit 13 is, for example, a microcomputer. The wavelength shift amount and the concentration of the target substance captured on the reflection surface 29 of the metal-film coated photonic crystal 21 have a correlation. Therefore, the processing unit 13 can obtain the concentration of the target substance captured on the reflection surface 29 from the wavelength shift amount.

(Method of Detecting Target Substance)

Next, a method of detecting the target substance (target substance detection method) using the target substance detecting device 10 illustrated in FIG. 1 will be explained. In this example, a case in which a cortisol antibody is absorbed by the reflection surface 29 of the metal-film coated photonic crystal 21, and cortisol in saliva is detected/measured as the target substance to be detected will be explained. As the photonic crystal 25, one obtained such that a cycloolefin-based polymer sheet having surface on which a predetermined microstructure is formed by heat nanoimprint, is cut into a predetermined size, is used.

Figure 26:
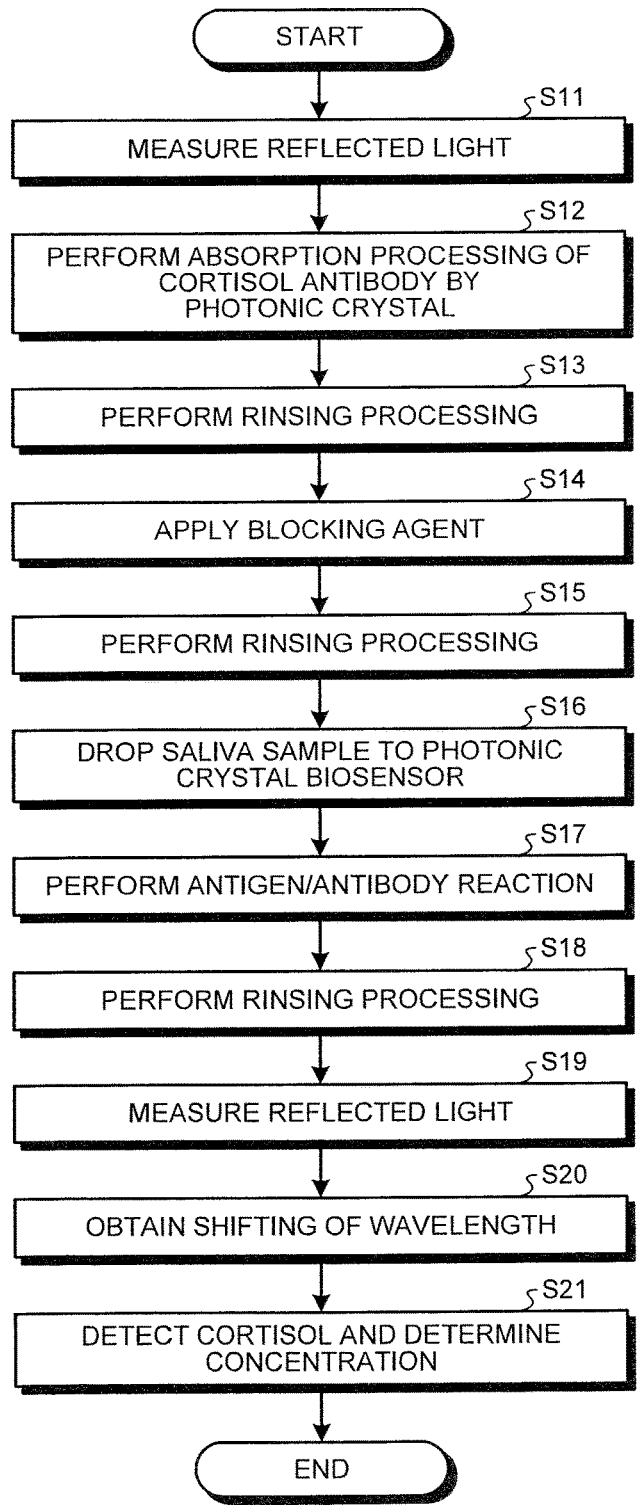
FIG. 26 is a flowchart of a method of detecting a target substance.

FIG. 26 is a flowchart illustrating an example of a method of detecting a target substance according to the first embodiment. First, in step S11, the photo-detection section 12 detects reflected light LR from the reflection surface 29 of when the reflection surface 29 of the photonic crystal 25 is irradiated with light, and the processing unit 13 measures the reflected light LR (step S11). The processing unit 13 measures a spectrum of the reflected light intensity of the reflected light LR. The wavelength of the light (incident light LI) irradiating the reflection surface 29 is, for example, from 300 nm to 2000 nm, both inclusive.

Next, in step S12, a cortisol antibody solution (cortisol antibody concentration 1 to 50 μg/ml) is dropped on the reflection surface 29 of the metal-film coated photonic crystal 21. Then, the photonic crystal biosensor 11 is brought to stand still for a predetermined time, or at a predetermined temperature for a predetermined time, as needed, and the cortisol antibody is absorbed by the reflection surface 29 of the metal-film coated photonic crystal 21.

Next, in step S13, phosphate buffered saline (PBS) is dropped on the reflection surface 29 of the metal-film coated photonic crystal 21. Following that, rinsing processing that performs removal using centrifugal force or the like is performed several times.

Next, in step S14, skim milk is dropped on the reflection surface 29 of the photonic crystal 25, as a blocking agent 35. The photonic crystal biosensor 11 is brought to stand still for a predetermined time, or at a predetermined temperature for a predetermined time, as needed, and the skim milk is absorbed in a non-absorption portion of the cortisol antibody on the reflection surface 29 of the metal-film coated photonic crystal 21.

Following that, in step S15, rinsing processing with the phosphate buffered saline is performed several times, similarly to the rinsing processing (step S13). With the above operation, predetermined processing is applied to the reflection surface 29 of the metal-film coated photonic crystal 21, and the photonic crystal biosensor 11 is formed.

Next, in step S16, first, saliva as a solution containing cortisol is prepared. Sampling of the saliva and pretreatment such as removal of impurities are performed using a commercially available saliva collecting kit. The preparation of the saliva can be performed at any time before the saliva is dropped on the photonic crystal biosensor 11. For example, the preparation of the saliva may be performed before the formation of the photonic crystal biosensor 11, may be performed in parallel with the formation of the photonic crystal biosensor 11, or may be performed after the measurement of the reflected light intensity. 10 μL to 50 μL of the saliva subjected to the sampling and the pretreatment is dropped on the photonic crystal biosensor 11.

Next, in step S17, the photonic crystal biosensor 11 is brought to stand still for a predetermined time, or at a predetermined temperature for a predetermine time, as needed, and the antigen antibody reaction is performed.

Following that, in step S18, rinsing processing with the phosphate buffered saline is performed several times, similarly to the rinsing processing (step S15).

Next, in step S19, the reflection surface 29 of the metal-film coated photonic crystal 21 is irradiated with light, using the target substance detecting device 10. The irradiated light of this time is the same as the light irradiating the reflection surface 29 in step S11. Then, the target substance detecting device 10 measures the spectrum of the reflected light intensity of the reflected light LR from the reflection surface 29.

The wavelength in the extreme value of the reflected light intensity of the photonic crystal biosensor 11 is changed, by being subject to an influence of the antigen/antibody reaction on the reflection surface 29 or in the vicinity of the reflection surface 29. Therefore, cortisol in the saliva can be detected from a difference between the wavelengths in the extreme value of the reflected light intensity before and after the reaction, that is, the wavelength shift amount. Further, the concentration of cortisol in the saliva can be obtained from the wavelength shift amount.

In step S20, the processing unit 13 obtains shifting (wavelength shift amount) of the wavelength in the extreme value (minimum value) of the reflected light intensity (or the reflectance) measured in step S19. The wavelength shift amount is, for example, a difference $\lambda 2-\lambda 1$ between the wavelength $\lambda 2$ after the target substance is captured on the reflection surface 29, and the wavelength $\lambda 1$ corresponding to the extreme value (minimum value) of the reflected light intensity (or the reflectance) when the target substance is not captured on the reflection surface 29.

In step S21, the processing unit 13 determines that cortisol exists in the saliva, when there is a predetermined amount or more of the wavelength shift amount. Further, the processing unit 13 determines the concentration of cortisol, using a relational expression between the wavelength shift amount and the concentration of cortisol, based on the wavelength shift amount. At this time, the relational expression is obtained in advance, and is stored in a storage unit of the processing unit 13.

In the above-described example, the wavelength shift amount is obtained using the wavelength of the extreme value of the reflected light intensity on the reflection surface 29 in a state where the target substance is not captured. However, an embodiment is not limited to the example. For example, the wavelength shift amount may be obtained using the wavelength of the extreme value of the reflected light intensity from the reflection surface 29 of after the rinsing processing (step S13 or S15) is completed. Further, in steps S11 and S19, when there is a plurality of extreme values, an extreme value to be focused is appropriately selected. Then, the wavelength $\lambda 1$ and the wavelength $\lambda 2$ are obtained about the selected extreme value.

Note that, in the first embodiment, in the metal-film coated photonic crystal 21, the antibody 34 is fixed to the reflection surface 29. However, an embodiment is not limited to the embodiment, and the metal-film coated photonic crystal 21 may be used without fixing the antibody 34 to the reflection surface 29.

[Second Embodiment]

A target substance detecting device including a target substance capturing device according to a second embodiment will be explained. The target substance capturing device according to the second embodiment is similar to that of the first embodiment, except a change that an antigen (target substance) 36 is fixed to a reflection surface 29 of a metal-film coated photonic crystal 21, and an antibody 34 is absorbed by the antigen 36, and thus overlapping description is omitted.

FIGS. 27 to 31 are diagrams for describing a principle of a photonic crystal biosensor. Description will be given using cortisol as the antigen 36, and an anti-cortisol antibody as the antibody 34, in the second embodiment, as a special reaction between the antibody 34 and the antigen 36.

Figure 27:
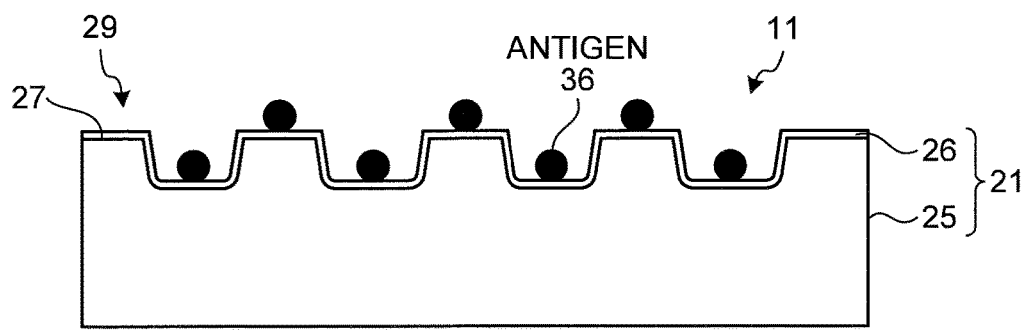
FIG. 27 is a diagram for describing a principle of a photonic crystal biosensor.

First, as illustrated in FIG. 27, as a means for fixing the antigen 36 to the reflection surface 29a of the metal-film coated photonic crystal biosensor 11, the metal-film coated photonic crystal biosensor 11 can perform the means for fixing the antigen 36 similarly to fixing the antibody 34 to the reflection surface 29. Examples of the means for fixing the antigen 36 to the reflection surface 29 include chemical bond and physical bond methods such as covalent bond, chemisorption, and physisorption. These means can be appropriately selected according to the nature of the antigen 36.

The amount of the antigen 36 fixed to the metal-film coated photonic crystal 21 is constant. Therefore, when the antibody 34 is absorbed by the antigen 36 fixed to the metal-film coated photonic crystal 21 and a complex 65 (see FIGS. 29 and 30) is formed, the photonic crystal biosensor 11 can output a physical amount that correlates with the amount of the formed complex 65. The constant amount of the fixed antigen 36 may be appropriately changed, and can be set to an optimum amount according to a range of the amount of the antigen 36 contained in a sample S, for example.

Figure 28:
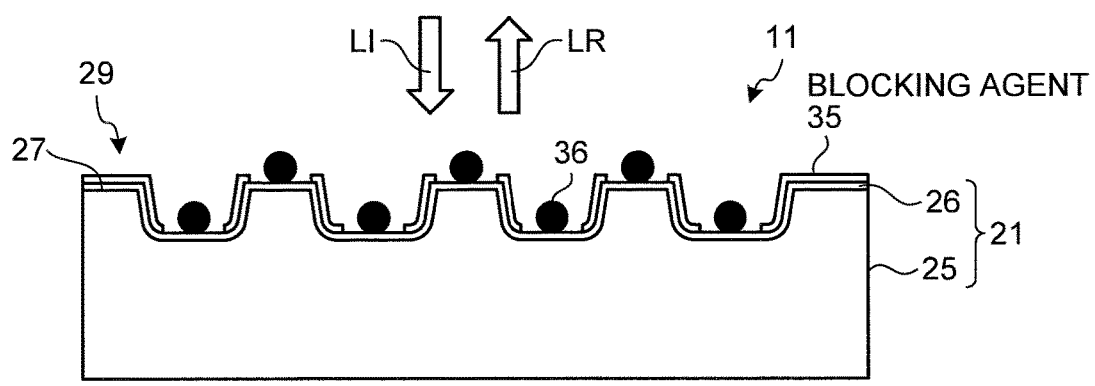
FIG. 28 is a diagram for describing a principle of a photonic crystal biosensor.

Following that, as illustrated in FIG. 28, a blocking agent 35 is fixed to a place of the reflection surface 29, where the antigen 36 is not attached.

Next, the reflection surface 29 of a photonic crystal 25 is irradiated with light (incident light) LI of from 300 nm to 900 nm, both inclusive, in parallel light, and such that the optical axis is perpendicular to the reflection surface 29. A wavelength with which the intensity or the reflectance of reflected light LR of this time becomes the extreme value (the minimum value in this example) is $\lambda 1$.

Figure 29:
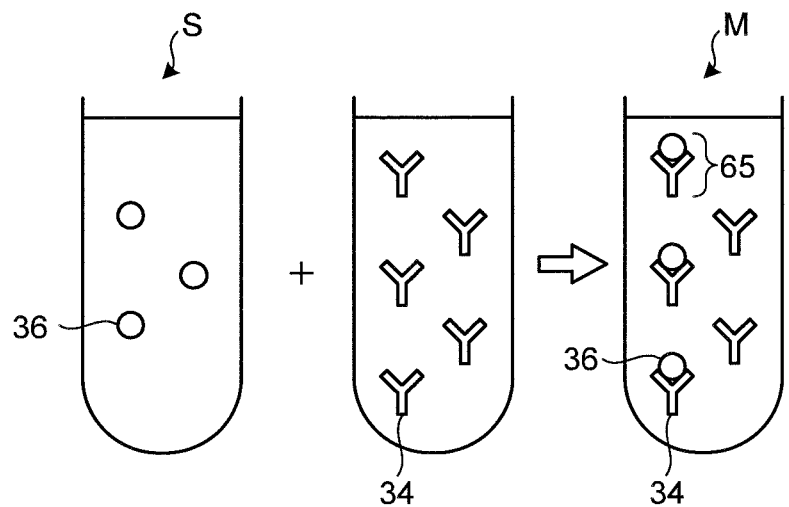
FIG. 29 is a diagram for describing a principle of a photonic crystal biosensor.
Figure 30:
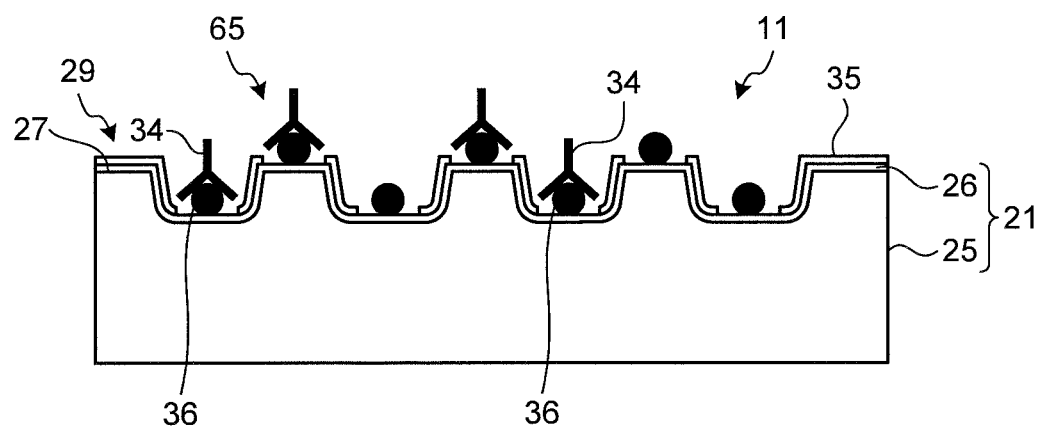
FIG. 30 is a diagram for describing a principle of a photonic crystal biosensor.
Figure 31:
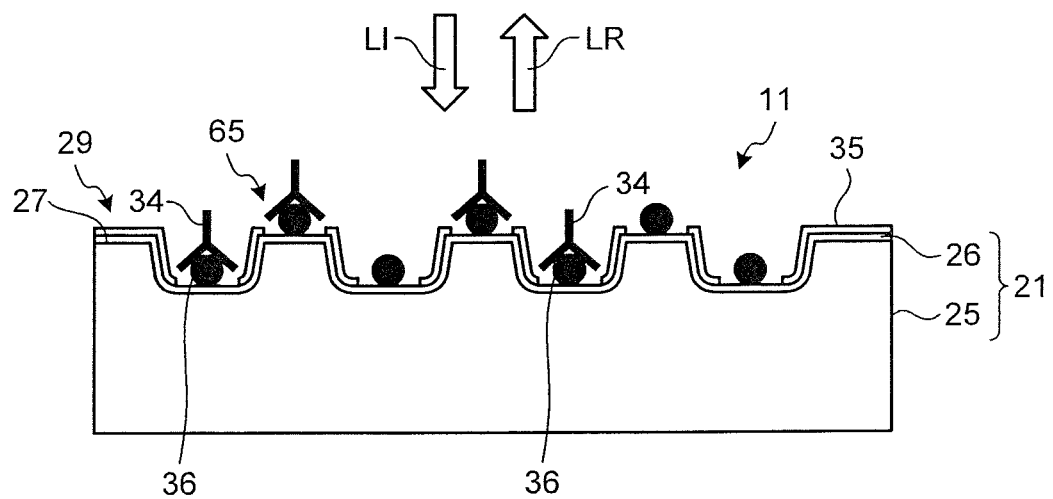
FIG. 31 is a diagram for describing a principle of a photonic crystal biosensor.

Next, as illustrated in FIG. 29, a mixture M that contains the complex 65 of the antigen 36 and the antibody 34, and the antibody 34 is prepared. The mixture M can be obtained such that the sample S that contains the antigen 36 and a solution that contains a known amount of the antibody 34 are mixed. The complex 65 can be obtained such that the sample S that contains the antigen 36, and the solution that contains a known amount of the antibody 34 are mixed, and the antibody 34 and the antigen 36 react with each other. The antibody 34 remains without having a reaction with the antigen 36 in the mixture M, by causing the known amount of the antibody 34 to be larger than the amount of sites to be combined with the antigen 36 contained in the known amount of the sample S. The mixture M is brought to come in contact with the reflection surface 29 of the metal-film coated photonic crystal 21. Accordingly, as illustrated in FIG. 30, the complex 65 is formed on the reflection surface 29 by the antigen 36 fixed to the reflection surface 29 and the antibody 34. Following that, as illustrated in FIG. 31, the reflection surface 29 of the metal-film coated photonic crystal 21 is irradiated with the light (incident light) LI of from 300 nm to 2000 nm, both inclusive, in parallel light, and such that the optical axis is perpendicular to the reflection surface 29. A wavelength with which the reflected light intensity or the reflectance of the reflected light LR of this time becomes the extreme value (the minimum value in this example) is $\lambda 2$.

The wavelength shift amount of the wavelength with which the reflectance of light becomes the extreme value is $\lambda 2-\lambda 1$. The wavelength shift amount is changed according to change of a surface state on the reflection surface 29 of the metal-film coated photonic crystal 21. Detection and quantification of the antigen 36 are performed based on the wavelength shift amount. The photonic crystal biosensor 11 outputs an optical physical amount. This physical amount correlates with the change of the surface state on the reflection surface 29, and correlates with the amount of the complex 65 formed by the antigen 36 fixed to the reflection surface 29 and the antibody 34.

In the second embodiment, cortisol as the antigen 36 is fixed to the metal-film coated photonic crystal 21, and the anti-cortisol as the antibody 34 is brought to react with cortisol. The change of the surface state of the metal-film coated photonic crystal 21 becomes large, and the sensitivity of the photonic crystal biosensor 11 is improved, in the case like the second embodiment in which the anti-cortisol antibody is brought to react with cortisol after cortisol is fixed to the reflection surface 29 of the metal-film coated photonic crystal 21, compared with the case like the first embodiment in which the antigen 36 is brought to react with the antibody 34 after the antibody 34 is fixed to the reflection surface 29 of the metal-film coated photonic crystal 21.

Next, a method of measuring the concentration of the antigen 36 will be explained. An amount of a site to be combined of the antigen 36 contained in the sample S is X, and the known amount of the antibody 34 in the mixture M is C. With regard to the relationship between X and C, X is made smaller than C (X<C). In the mixture M, the antigen 36 and the antibody 34 have an antigen/antibody reaction, and the complex 65 is formed. Since X is smaller than C (X<C), the amount of the antibody 34 in the mixture M becomes C−X. Then, when the mixture M is brought to come in contact with the reflection surface 29 to which a constant amount of the antigen 36 is fixed, the antibody 34 in the mixture M has the antigen/antibody reaction with the antigen 36 of the reflection surface 29, so that the complex 65 is formed. The amount of the antigen 36 fixed to the reflection surface 29 is equal to or more than the amount C−X of the antibody 34 in the mixture M.

When all of the antibodies 34 in the mixture M have the antigen/antibody reaction with the antigen 36 of the reflection surface 29, the amount of the complex 65 becomes C−X. A wavelength shift amount Δλ obtained from the wavelengths λ1 and λ2 measured before and after the mixture M is brought to come in contact with the reflection surface 29 corresponds to the amount of the complex 65 fixed to the reflection surface 29. Therefore, Δλ=k×(C−X) is satisfied. k is a constant for converting the wavelength shift amount Δλ into the amount of the complex 65. The relationship between the amount of the complex 65 fixed to the reflection surface 29 and the wavelength shift amount Δλ is obtained in advance. From the above relational expression, the amount X of the antigen 36 can be obtained by C−Δλ/k. The concentration of the antigen 36 can be obtained based on the amount X of the antigen 36.

Further, in the second embodiment, the photonic crystal biosensor 11 may cause, as a complex binding substance, a secondary antibody, which specially reacts with the complex 65, to react with the complex 65 fixed to the reflection surface 29 of the metal-film coated photonic crystal 21. An excessive amount of the secondary antibody than that of the complex 65 is brought to come in contact with the reflection surface 29 of the metal-film coated photonic crystal 21. Then, the secondary antibody is attached to all of the complexes 65 to obtain a second complex. In doing so, the change of the surface state of the metal-film coated photonic crystal 21 becomes larger. As a result, the sensitivity of the photonic crystal biosensor 11 is further increased. The secondary antibody can be used as it is, or may be used by being added another substance. The change of the surface state of the metal-film coated photonic crystal 21 becomes larger as the secondary antibody is larger. Therefore, after another substance is added to the secondary antibody, the secondary antibody is brought to react with the complex 65, so that the sensitivity of the photonic crystal biosensor 11 is further increased.

When the second complex is formed on the reflection surface 29, the reflection surface 29 of after the second complex is formed is irradiated with light. A wavelength with which the reflected light intensity or the reflectance obtained as a result becomes the extreme value (the minimum value in this example) is λ2. When there is a plurality of extreme values, an extreme value to be focused is appropriately selected. The wavelength λ1 and the wavelength λ2 are obtained about the selected arbitrary extreme value. The photonic crystal biosensor 11 outputs an optical physical amount. This physical amount correlates with the change of the surface state on the reflection surface 29, and correlates with the amount of the second complex fixed to the reflection surface 29. Accordingly, the second complex is detected and quantified. The amount of the second complex is the same as the amount of the complex 65. Therefore, the complex 65 can be quantified.

[Third Embodiment]

Figure 33:
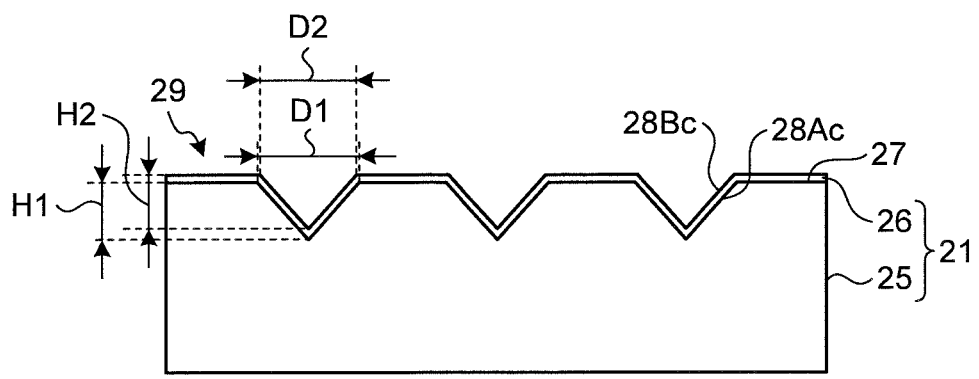
FIG. 33 is a cross-sectional view of a metal-film coated photonic crystal according to a third embodiment, the cross-sectional view being cut in a plane perpendicular to a reflection surface.

FIG. 33 is a cross-sectional view of a metal-film coated photonic crystal according to a third embodiment cut in a plane perpendicular to a reflection surface. As illustrated in FIG. 33, in the third embodiment, non-flat portions 28Ac and 28Bc are conically recessed portions depressed in a surface 27. Accordingly, when a metal-film coated photonic crystal 21 is manufactured using a die and a resin, by heat nanoimprint, the die can be easily released from the resin. Therefore, the non-flat portions 28Ac and 28Bc can be more easily formed than the non-flat portions 28A and 28B that are the columnar recessed portions of the first embodiment. Therefore, the metal-film coated photonic crystal 21 according to the third embodiment can be easily manufactured.

Note that, in the above description, the non-flat portion according to the third embodiment is the recessed portion as illustrated in FIG. 33. However, the non-flat portion may be a protruding portion. The non-flat portions 28Ac and 28Bc of this time are a conical protruding portion protruding from the surface 27.

Further, cross section shapes of the non-flat portions 28Ac and 28Bc along the reflection surface 29 may be a circular shape, may be a hexagonal shape as illustrated in FIG. 32A or a star shape as illustrated in FIG. 32B. When the cross section shapes of the non-flat portions 28Ac and 28Bc along the reflection surface 29 are the hexagonal shape, the non-flat portions 28Ac and 28Bc are a hexagonal pyramid recessed portion depressed in the surface 27. When the cross section shapes of the non-flat portions 28Ac and 28Bc along the reflection surface 29 are the star shape, the non-flat portions 28Ac and 28Bc are a pyramid recessed portion with a star-shaped bottom surface depressed in the surface 27.

Next, a performance index of the sensitivity of the photonic crystal biosensor 11 will be specifically explained. When a photonic crystal substrate using an uneven shape (hereinafter, "nano-cycle structure") having nanometer-order cyclicity on a surface is irradiated with light, a surface plasmon resonance phenomenon occurs, and a spectrum of reflected light exhibits a peak wavelength $\lambda_{peak}$ depending on the material and the structure. The peak wavelength $\lambda_{peak}$ is expressed by the following expression, where a cycle is d, a dielectric constant of metal is $\varepsilon_m$, a refractive index of an environment is n, and orders of diffraction are i and j.

$$\lambda_{peak} = \frac{\sqrt{3}\,d}{2(i^2 + j^2 - ij)^{1/2}} \left[ \frac{\varepsilon_m n^2}{\varepsilon_m + n^2} \right]^{1/2} \quad (1)$$

Assume that the material of the metal and the cycle of the nano-cycle structure are constant, sensitivity S (nm/RIU) defined by a peak wavelength shift $\Delta\lambda_{peak}$ with respect to refractive index change Δn of an environment can be obtained by differentiating the (Expression 1) with the refractive index n of an environment, and can be expressed by (Expression 2), and it is found that the sensitivity S is proportional to the cycle d (nm).

$$S = \frac{\Delta \lambda_{peak}}{\Delta n} = \frac{d\lambda_{peak}}{dn} = \frac{\sqrt{3}\,d}{2(i^2 + j^2 - ij)^{1/2}} \left[\frac{\varepsilon_m}{\varepsilon_m + n^2}\right]^{3/2} \quad (2)$$

The sensitivity S increases with the peak wavelength to be used or the cycle, and the half-value width (full wavelength at half maximum: FWHM unit nm) of the spectrum shape is also increased with the peak wavelength to be used. Therefore, a sensitivity figure of merit FOM1 is used as a performance index of sensitivity (Prior Art 3).

$$FOM1 = \frac{S}{FWHM} \quad (3)$$

Further, to accurately identify the peak wavelength, a sharp peak shape is desired. Therefore, a sensitivity figure of merit FOM2 obtained by dividing the height of the spectrum (full height: FH) with the half-value width is used (Prior Art 3).

$$FOM2 = \frac{FH}{FWHM} \times 1000 \quad (4)$$

A sensor substrate having high FOM1 and FOM2 values can be said to be a highly sensitive sensor substrate having a high S/N ratio. Typically, in a biosensor, a wavelength that exhibits an extreme value in a spectrum of reflected light of light incident on a surface of a sensor depends on a cycle of a lattice pattern formed by unevenness according to a nano-cycle structure of the surface of the sensor. Therefore, to detect a wavelength having a specific length included in the reflected light, it is desirable to cause the cycle of the lattice pattern of the reflection surface to be a desired value.

Meanwhile, to enhance the sensor sensitivity, dense arrangement of the unevenness is effective. However, if the unevenness is simply densely arranged, the cycle of the lattice pattern of the reflection surface becomes small, and thus there is a problem that measurement of the wavelength becomes difficult. To respond to the problem, conventionally, there are many measures that focus only on improvement of the sensitivity S, by making the cycle of the recessed portions large after forming the recessed portions having a circular cross section, as an uneven structure. However, there are small number of measures that consider the spectrum shape of the reflected light.

For example, Prior Art 1 describes a biosensor in which columnar protruding portions are arrayed in a uniform square lattice shape, as the uneven structure, that is, which includes a reflection surface having arrangement of one rotational symmetry. In such a sensor, lattice spacing is determined in accordance with a wavelength to be measured, and thus when the lattice spacing is relatively large, the protruding portions have a sparse arrangement, and the FOM2 value is decreased.

Meanwhile, in a case of an uneven arrangement in which a lattice pattern having a large cycle and a lattice pattern having a small cycle are mixed, that is, having a plurality of rotational symmetries, a plurality of extreme values are caused in the spectrum of the reflected light. In this case, if measurement can be performed using any of the plurality of extreme values, a proper output can be obtained as a sensor, and thus a sensor that can detect existence/non-existence of a target substance with high reliability can be obtained. On the other hand, individual extreme value becomes small. Therefore, accurate measurement of the amount of the target substance may be difficult. Hereinafter, the photonic crystal biosensor according to the above-described embodiment being able to accurately measure the amount of the target substance will be explained.

Figure 34:
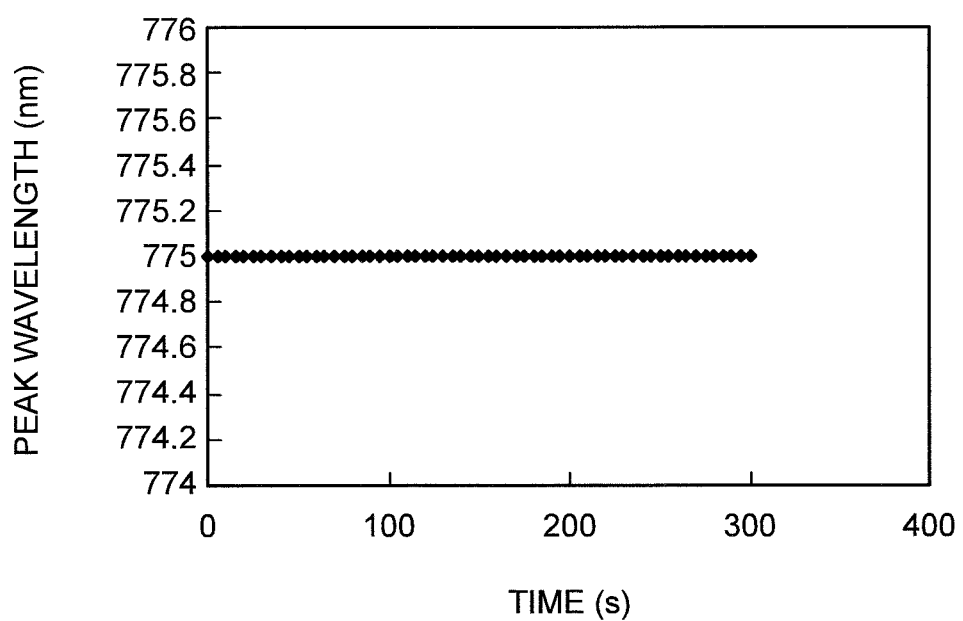
FIG. 34 is a diagram illustrating a peak wavelength of a spectrum of reflected light of when a photonic crystal biosensor according to a first example is irradiated with light.
Figure 35:
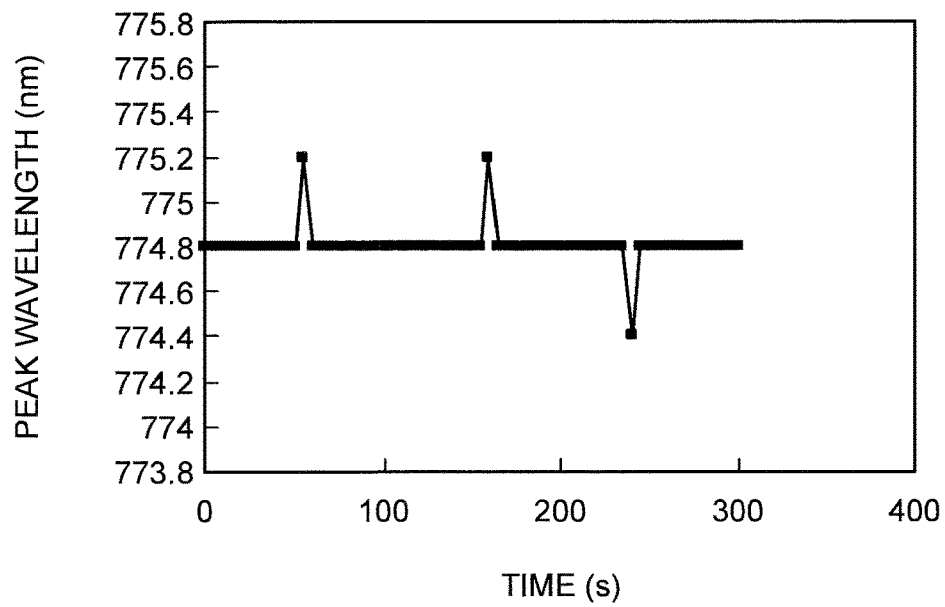
FIG. 35 is a diagram illustrating a peak wavelength of a spectrum of reflected light of when a photonic crystal biosensor according to a first comparative example is irradiated with light.

FIG. 34 is a diagram illustrating a peak wavelength of a spectrum of reflected light of when a photonic crystal biosensor according to a first example is irradiated with light. FIG. 35 is a diagram illustrating a peak wavelength of a spectrum of reflected light of when a photonic crystal biosensor according to a first comparative example is irradiated with light. FIGS. 34 and 35 illustrate results of measurement that has been performed for 300 seconds, of the peak wavelength in a spectrum of reflected light of light that has been irradiating the photonic crystal biosensor. The photonic crystal biosensor according to the first example is the photonic crystal biosensor 11 described in the first embodiment. That is, the photonic crystal biosensor according to the first example includes the non-flat portions 28B that are columnar recessed portions depressed in the surface 27, and the unit arrays U arranged to form the lattice pattern La. In the non-flat portion 28B according to the first example, the diameter D2 illustrated in FIG. 4 is 150 nm, and the depth H2 is 200 nm. In contrast to the first example, the first comparative example is different in that the non-flat portions 28B are arranged such that one center G1 superposes the position of the intersection of the lattice pattern La, as illustrated in FIG. 5.

As illustrated in FIG. 34, the peak wavelength in the first example is constant during the 300 seconds. In contrast, as illustrated in FIG. 35, the peak wavelength in the first comparative example varies several times during the 300 seconds. That is, in the first comparative example, a noise can easily occur. The first example has a smaller half-value width in a spectrum shape of the reflected light than the first comparative example, and thus has a stable measurement result of the peak wavelength. Further, in the first example, the FOM1 value is 43.7, and the FOM2 value is 68.6. In the first comparative example, the FOM1 value is 42.0, and the FOM2 value is 59.8. Both of the FOM1 and FOM2 of the first example are higher than those of the first comparative example. Accordingly, it is found that the photonic crystal biosensor according to the first example has higher sensitivity as a sensor than the photonic crystal biosensor according to the first comparative example. Therefore, the photonic crystal biosensor 11 according to the first embodiment can enhance the sensor sensitivity, compared with the conventional technology, and thus can accurately measure the amount of the target substance.

Figure 36:
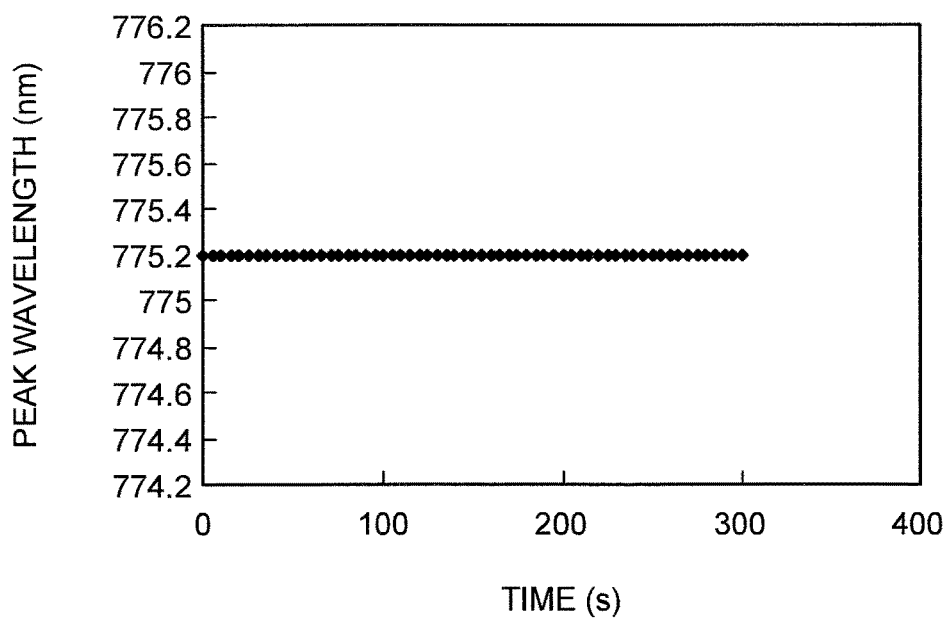
FIG. 36 is a diagram illustrating a peak wavelength of a spectrum of reflected light of when a photonic crystal biosensor according to a second example is irradiated with light.
Figure 37:
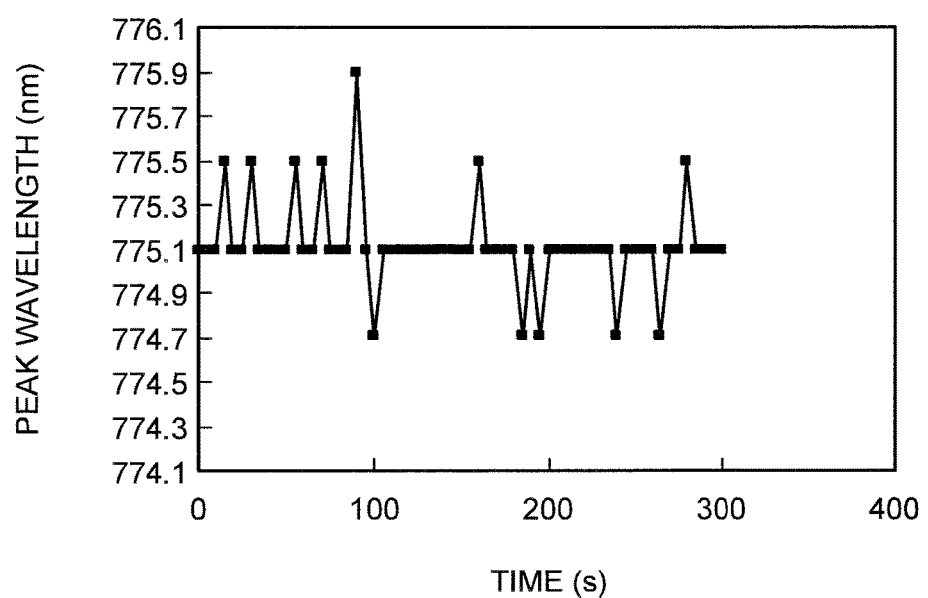
FIG. 37 is a diagram illustrating a peak wavelength of a spectrum of reflected light of when a photonic crystal biosensor according to a second comparative example is irradiated with light.

FIG. 36 is a diagram illustrating a peak wavelength of a spectrum of reflected light of when a photonic crystal biosensor according to a second example is irradiated with light. FIG. 37 is a diagram illustrating a peak wavelength of a spectrum of reflected light of when a photonic crystal biosensor according to a second comparative example is irradiated with light. FIGS. 36 and 37 illustrate results of measurement that has been performed for 300 seconds, of the peak wavelength in a spectrum of a reflected light of light that has been irradiating the photonic crystal biosensor. The photonic crystal biosensor according to the second example is the photonic crystal biosensor 11 described in the third embodiment. That is, the photonic crystal biosensor according to the second example includes the non-flat portions 28Bc that are conically recessed portions depressed in the surface 27, and the unit arrays U arranged to form the lattice pattern La. In the non-flat portion 28Bc according to the second example, the diameter D2 illustrated in FIG. 33 is 220 nm, and the depth H2 is 50 nm. In contrast to the second example, the second comparative example is different in that the non-flat portions 28B are arranged such that one center G1 superposes the position of the intersection of the lattice pattern La, as illustrated in FIG. 5.

As illustrated in FIG. 36, the peak wavelength in the second example is constant during the 300 seconds. In contrast, as illustrated in FIG. 37, the peak wavelength in the second comparative example varies several times during the 300 seconds. That is, in the second comparative example, a noise easily occurs. The second example has a smaller half-value width of a spectrum shape of reflected light than the second comparative example, and has a stable measurement result of the peak wavelength. Further, in the second example, the FOM1 value is 54.4, and the FOM2 value is 65.9. In the second comparative example, the FOM1 value is 42.0, and the FOM2 value is 32.5. Both of the FOM1 and FOM2 of the second example are higher than those of the second comparative example. Accordingly, it is found that the photonic crystal biosensor according to the second example has higher sensitivity as a sensor than the photonic crystal biosensor according to the second comparative example. Therefore, the photonic crystal biosensor 11 according to the third embodiment can enhance the sensor sensitivity, compared with the conventional technology, and thus can accurately measure the amount of the target substance. Further, the photonic crystal biosensor 11 according to the third embodiment can be easily manufactured.

REFERENCE SIGNS LIST

10 Target substance detecting device
11 Photonic crystal biosensor (target substance capturing device)
12 Photo-detection section
13 Processing unit
21 Metal-film coated photonic crystal
22 Upper plate
23 Lower plate
24 and 43 Opening
25 Photonic crystal
26 Metal film
27 Surface
28A and 28B Non-flat portion
29 Reflection surface
34 Antibody (target substance capturing material)
35 Blocking agent (protecting substance)
36 Antigen (target substance)
37 and 65 Complex
38 and 44 Liquid drop holding portion
39 Magnet sheet
41 Hole-opened cover
42 Sheet
51 Light source
52 Measuring probe
53 Photo-detection device
54 First optical fiber
55 Second optical fiber
56 Collimating lens
61 Emission surface
62 Incident surface
63 Same surface (incident/emission surface)
M Mixture
U Unit array
LI Incident light
LR Reflected light

The invention claimed is:

1. A target substance capturing device that captures a target substance with a biosensor using a photonic crystal including a reflection surface that reflects irradiated light, and having a plurality of non-flat portions arrayed on the reflection surface, wherein
    each of the non-flat portions belongs to one of a plurality of unit arrays in which the non-flat portions are arranged such that a center of each of the non-flat portions superposes a position of a vertex of a regular triangle, each unit array of the unit arrays being a respective unit triangle of a plurality of unit triangles, the plurality of unit triangles forming a lattice pattern, the unit arrays are arranged in such a manner that:
    the non-flat portions belonging to the one of the unit arrays are different from the non-flat portions belonging to the unit arrays adjacent to the one of the unit arrays;
    each unit triangle has a g-center that is a center of gravity that superposes an intersection of the lattice pattern, the lattices intersecting with each other at an angle of 60°;
    the lattice pattern has a lattice cycle of a distance that is a distance between the g-centers adjacent each other;
    the non-flat portions are not arranged in flat-center positions, each of which is a center of gravity of a triangle that is made by connecting the g-centers of adjacent three of the unit triangles having sides that are parallel to straight lines included in the lattice pattern;
    each of the flat-center positions are adjacent to and surrounded by three pairs of the non-flat portions, each pair of the three pairs of non-flat portions belonging to a respective one of the unit arrays; and
    the non-flat portions are arranged in at least two pairs of adjacent rows on the reflection surface, each pair of the adjacent rows comprising a first row and a second row, wherein the second row has two times as many of the non-flat portions as the first row.

2. The target substance capturing device according to claim 1, wherein a cross section of the non-flat portion along the reflection surface is a circle, and a c-diameter that is a diameter of the cross section of the non-flat portion is one times or less a c-distance that is a length between centers of the non-flat portions belonging to the unit triangle of one of the unit arrays.

3. The target substance capturing device according to claim 1, wherein a cross section of the non-flat portion along the reflection surface is a regular hexagon or a star shape.

4. The target substance capturing device according to claim 2, wherein:
    the c-diameter is 0.25 times or less the lattice cycle and,
    the c-diameter is in a range from 50 nm to 1000 nm,
    the c-distance is in a range from 100 nm to 2000 nm.

5. The target substance capturing device according to claim 4,
    the c-diameter is in a range from 100 nm to 500 nm.

6. The target substance capturing device according to claim 4, the c-distance is in a range from 200 nm to 1000 nm.

7. The target substance capturing device according to claim 1, wherein
    for at least one of the first rows of the non-flat portions, a respective one of the flat-center positions is arranged directly between each of the non-flat portions in the first row.

* * * * *